(12) United States Patent
Huizing et al.

(10) Patent No.: US 9,341,619 B2
(45) Date of Patent: *May 17, 2016

(54) HYPOSIALYLATION DISORDERS

(71) Applicants: THE UNITED STATES OF AMERICA, as represented by the Secretary, Department of Health and Human Services, Washington, DC (US); Emory University, Atlanta, GA (US)

(72) Inventors: Marjan Huizing, Santa Cruz, CA (US); William A. Gahl, Kensington, MD (US); Nuria Carrillo-Carrasco, Bethesda, MD (US); Miao He, Alpharetta, GA (US); Xueli Li, Tucker, GA (US); Rong Jiang, Tucker, GA (US)

(73) Assignees: The United States of America, as represented by the Secretary, Department of Health and Human Services, Washington, DC (US); Emory University, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/208,570

(22) Filed: Mar. 13, 2014

(65) Prior Publication Data
US 2014/0271615 A1 Sep. 18, 2014

Related U.S. Application Data

(60) Provisional application No. 61/785,094, filed on Mar. 14, 2013.

(51) Int. Cl.
*G01N 33/53* (2006.01)
*G01N 33/68* (2006.01)

(52) U.S. Cl.
CPC ........ *G01N 33/5308* (2013.01); *G01N 33/6893* (2013.01); *G01N 2800/04* (2013.01)

(58) Field of Classification Search
None
See application file for complete search history.

(56) References Cited

U.S. PATENT DOCUMENTS

| | | | |
|---|---|---|---|
| 8,410,063 | B2 | 4/2013 | Huizing et al. |
| 2011/0212917 | A1 | 9/2011 | Shiota et al. |
| 2012/0276560 | A1 | 11/2012 | Kakkis et al. |
| 2013/0058998 | A1 | 3/2013 | Huizing et al. |
| 2013/0109637 | A1 | 5/2013 | Kakkis et al. |

FOREIGN PATENT DOCUMENTS

| | | |
|---|---|---|
| WO | WO 2008/150477 | 12/2008 |
| WO | WO 2012/082830 A1 | 6/2012 |
| WO | WO 2012/083228 | 6/2012 |

OTHER PUBLICATIONS

Waiker et al (J Am Soc Nephrol. Jan. 2012; 23(1): 13-21).*
Kuzmanov et al (.BMC Medicine 2013, 11:31).*
Broccolini et al., "Analysis of NCAM Helps Identify Unusual Phenotypes of Hereditary Inclusion-Body Myopathy," Neurology 75: 265-272 (2010) (abstract only).
Hanisch and Baldus, "The Thomsen-Friedenreich (TF) Antigen: A Critical Review on the Structural, Biosynthetic and Histochemical Aspects of a Pancarcinoma-Associated Antigen," Histol. Histopathol 12: 263-281 (1997).
Ju et al., "The Tn Antigen-Structural Simplicity and Biological Complexity," Angew. Chem. Int. Ed. 50:1770-1791 (2011).
Kakani, "The Gne M712T Mouse as a Model for Human Glomerulopathy," American Journal of Pathology 180(4):1431-1440 (Apr. 2012).
Liu et al., "N- and O-Linked Glycosylation of Total Plasma Glycoproteins in Galactosemia," Mol. Genet. 106:442-452 (2012).
Nemoto-Sasaki et al., Correlation Between the Sialylation of Cell Surface Thomsen-Friedenreich Antigen and the Metastatic Potential of Colon Carcinoma Cells in a Mouse Model, Glycoconi J. 18:895-906 (2001)(abstract only).
Niethamer et al., "Oral Monosaccharide Therapies to Reverse Renal and Muscle Hyposialylation in a Mouse Model of GNE Myopathy," Molecular Genetics and Metabolism 4C(6):1-8 (2012).
Sotozono et al, "The Thomsen-Friedenreich Antigen-Related Carbohydrate Antigens in Human Gastric Intestinal Metaplasia and Cancer," Journal of Histochemistry & Cytochemistry 42(12):1575-1584 (1994).
Valles-Ayoub et al., Serum Neural Cell Adhesion Molecule is Hyposialylated in Hereditary Inclusion Body Myopathy, Genet. Test Mol. Biomarkers 16:313-317, (2012)(abstract only).
Xia et al., "Serum N-Glycan and O-Glycan Analysis by Mass Spectrometry for Diagnosis of Congenital Disorders of Glycosylation," Analytical Biochemistry 442(2):178-85 (2013).
Huizing and Krasnewich, "Hereditary Inclusion Body Myopathy: A Decade of Progress," Biochim Biophys Acta. 1792(9): 881-887 (Sep. 2009).

(Continued)

*Primary Examiner* — Brian J Gangle
*Assistant Examiner* — Andrea McCollum
(74) *Attorney, Agent, or Firm* — Klarquist Sparkman, LLP

(57) ABSTRACT

Methods are disclosed for diagnosing a hyposialylation disorder. Methods are also disclosed for determining the effectiveness of a therapeutic agent for treatment of a hyposialylation disorder in a subject. These methods include measuring an amount of monosialylated Thomsen-Friedenreich (ST) antigen and measuring an amount of non-sialylated Thomsen-Friedenreich antigen (T) in a biological sample, such as a serum or plasma sample from the subject and determining the ratio of T to ST. A ratio of T to monosialylated ST of about 0.06 or higher diagnoses the hyposialylation disorder or indicates that the therapeutic agent is not effective for the treatment of the hyposialylation disorder. In other embodiments, a ratio of T to ST less than about 0.06 indicates that the therapeutic agent is effective for the treatment of the hyposialylation disorder, or the subject does not have the hyposialylation disorder. In additional embodiments, these methods can be used to determine the lowest effective dosage of the therapeutic agent of use to treat the subject.

19 Claims, 10 Drawing Sheets

(56) References Cited

OTHER PUBLICATIONS

International Search Report from PCT Patent Application No. PCT/US2014/025633, 4 pages (mailed Aug. 27, 2014).
Liu et al, "N- and O-linked Glycosylation of Total Plasma Glycoproteins in Galactosemia," *Mol Genet Metab.* 106(4):442-54 (Aug. 2012).
Marklova and Albahri, "Screening and Diagnosis of Congenital Disorders of Glycosylation," *Clin. Chim. Acta.* 385(1-2):6-20 (Oct. 26, 2006).
Written Opinion from PCT Patent Application No. PCT/US2014/025633, 6 pages (mailed Aug. 27, 2014).
Yu "The Oncofetal Thomsen-Friedenreich Carbohydrate Antigen in Cancer Progression," *Glycoconj J.* 24(8):411-20 (Apr. 25, 2007).

* cited by examiner

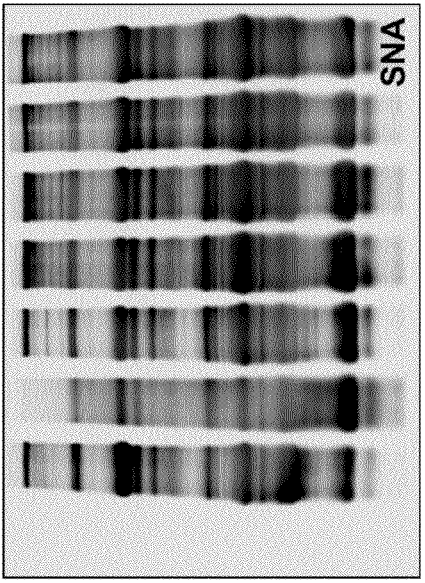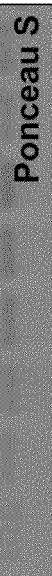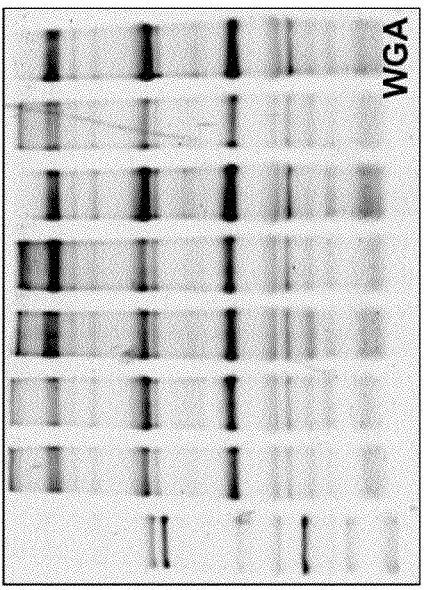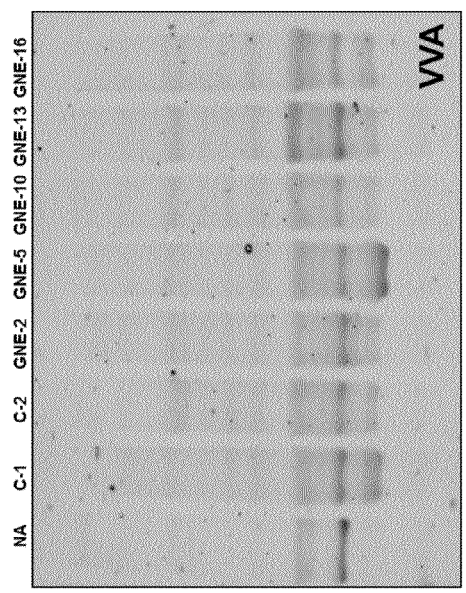

HYPOSIALYLATION DISORDERS

CROSS REFERENCE TO RELATED APPLICATION

This claims the benefit of U.S. Provisional Application No. 61/785,094, filed Mar. 14, 2013, which is incorporated herein by reference.

FIELD OF THE DISCLOSURE

This relates to the field of hyposialylation disorders, specifically to methods for diagnosing these disorders using the ratio of Thomsen-Friedenreich antigen (T) to monosialylated Thomsen-Friedenreich antigen (ST).

BACKGROUND

Sialic acid contains a net negative charge and is found on terminating branches of glycans, which include glycoproteins (with N- or O-linked glycosylation) and glycolipids (including glycosphingolipids or gangliosides). The sialic acid modification of cell surface molecules impacts protein structure and stability, regulation of cell adhesion, and signal transduction, amongst other processes.

Clinical diseases with a reduced amount of sialic acid bound to glycans are called "hyposialylation disorders." Hyposialylation can occur in a specific tissue or can be systemic. In some cases genetic defects cause hyposialylation disorders, but the etiology of many of these disorders is unknown.

One hyposialylation disorder associated with a genetic defect is GNE myopathy (also called HIBM, IBM type 2, Nonaka myopathy, or Distal Myopathy with Rimmed Vacuoles (DMRV)). GNE myopathy is caused by mutations in the GNE gene, encoding the key enzyme in sialic acid synthesis, the bifunctional enzyme UDP-N-acetylglucosamine-2-epimerase/N-acetylmannosamine kinase. Decreased GNE enzyme activity is believed to reduce sialic acid levels.

Other genetic disorders that may involve sialylation defects are the congenital disorders of glycosylation (CDGs). CDGs are a group of human genetic disorders characterized by alterations in glycoconjugates (Jaeken, *J Inherit Metab Dis* 2011, 34:853-858). A majority of the CDGs are caused by primary defects in the N- and/or O-glycosylation pathways that lead to defective glycan biosynthesis. In the past decade, about 60 genetic diseases have been identified that alter glycan synthesis and structure and ultimately the functions of many organ systems (He et al., The congenital disorders of glycosylation. In: *Laboratory Diagnosis of inherited Metabolic Diseases*. edn. Edited by Garg et al., Washington, D.C.: AACC Press; 2012: 179-199). CDG type I (CDG-I) disorders result from impaired synthesis of glycans, which may lead to unoccupied glycosylation sites on glycoproteins and glycolipids. CDG type II (CDG-II) disorders result from impaired processing of glycans, which lead to accumulation of glycoproteins and glycolipids with abnormal structures. CDG-II disorders also includes defects in chaperones and Golgi-trafficking complexes, such as defects in the conserved oligomeric Golgi complex (COG), dolichol synthesis, and CMP-sialic acid synthesis, which impair multiple glycosylation pathways including both N- and O-glycan synthesis and N-glycan processing (He et al., supra). Some multiple glycosylation defects may also present as mixed CDG-I and II (Pérez et al., *JIMD*, epub 2012; Perez et al., *JIMD* 2011, 1: 117-123; Mandato et al., *Pediatr Res* 2006, 59(2):293-298).

There is a need for non-invasive methods for the diagnosis of glycosylation disorders, including hyposialylation disorders, such as GNE myopathy and CDG disorders, and methods to determine the effectiveness of therapeutic agents for the treatment of hyposialylation disorders.

SUMMARY OF THE DISCLOSURE

Methods are disclosed for diagnosing a hyposialylation disorder. These methods include measuring an amount of monosialylated Thomsen-Friedenreich (ST) antigen, and measuring an amount of non-sialylated Thomsen-Friedenreich antigen (T) in a biological sample from the subject and determining the ratio of T to monosialylated ST.

In some embodiments, a ratio of T to monosialylated ST of about 0.06 or higher in a biological sample, such as a plasma or serum sample diagnoses the hyposialylation disorder. In other embodiments, a ratio of T to monosialylated ST of about 0.052 or higher in a biological sample, such as a plasma or serum sample diagnoses the hyposialylation disorder.

In other embodiments, the methods can include determining whether a subject will respond to a specific therapeutic agent, such as an agent that increases sialylation. In some examples, the methods include administering to the subject a therapeutic agent for the treatment of the hyposialylation disorder if the T to monosialylated ST in a plasma or serum sample is 0.06 or higher. In other examples, the methods include administering to the subject a therapeutic agent for the treatment of the hyposialylation disorder if the T to monosialylated ST in a plasma or serum sample is 0.052 or higher. The sample can be a plasma or a serum sample. The sample can be a tissue sample or cell extract.

In additional embodiments, a ratio of T to ST of less than about 0.06 indicates that the therapeutic agent is effective for the treatment of the hyposialylation disorder. In other embodiments, a ratio of T to ST of about 0.06 or greater indicates that the first dosage of the therapeutic agent is not effective for the treatment of the hyposialylation disorder. In further embodiments, a ratio of T to ST of less than about 0.052 indicates that the therapeutic agent is effective for the treatment of the hyposialylation disorder. In other embodiments, a ratio of T to ST of about 0.052 or greater indicates that the first dosage of the therapeutic agent is not effective for the treatment of the hyposialylation disorder.

In yet other embodiments, these methods can be used to determine the lowest effective dosage of the therapeutic agent of use to treat the subject. The sample can be a plasma or a serum sample. In additional embodiments, these methods can be used to determine the lowest effective dosage of the therapeutic agent of use to treat the subject. The sample can be a plasma or a serum sample. The sample can be a tissue sample or cell extract.

In some embodiments, methods are also disclosed for determining the effectiveness of a therapeutic agent for treatment of a hyposialylation disorder in a subject. These methods include measuring monosialylated Thomsen-Friedenreich (ST) antigen and measuring non-sialylated Thomsen-Friedenreich antigen (T) in a sample from the subject and determining the ratio of T to ST.

In some embodiments, the method is non-invasive. In specific, non-limiting examples of any of the methods disclosed herein, the sample is a plasma or serum sample. In other embodiments of any of the methods disclosed herein, this sample can be another tissue or cell sample, including but not limited to platelet, white cell, red cell, cerebrospinal fluid, urine, biopsy material from liver, kidney or muscle.

The foregoing and other features and advantages of the invention will become more apparent from the following detailed description of a several embodiments which proceeds with reference to the accompanying figures.

BRIEF DESCRIPTION OF THE FIGURES

FIG. 1A: Human normal plasma O-glycans were released by β-elimination and permethylated before the MALDI-TOF analysis. Measured m/z of each O-glycan are shown as well as their structures. FIG. 1B: the comparison of relative concentration of O-glycans between healthy control subjects and COG patients (compared to an internal standard (I.S.), raffinose at m/z 681). Control (n=10, shown in triangles), COG7 (n=2, shown in circles), COG4 (n=1, shown in circles). Monosaccharides in drawings of glycan structures: Black squares=GlcNAc, Grey circles=Gal, Black diamonds=Neu5Ac, Grey squares=GalNAc.

FIG. 2A: Chromatograph of multiple reaction monitoring (MRM) transitions for T-antigen (m/z 534/298) and monosialylated ST-antigen (m/z 895/520). FIG. 2B: MRM triggered enhanced product ion (EPI) profiles of T-antigen (top) and monosialylated ST-antigen (bottom). Multiple specific B and Y ion fragments were identified from these two O-glycan species in plasma total glycoprotein from normal controls, which confirms the specificity of the MRM transitions for each glycan. FIG. 2C: Linearity study of T-antigen quantification from a concentration range of 0.0625-5 μM. The correlation coefficient between the known standard concentration and measured concentration of T-antigen, $R^2$ is 1, with slope at 0.87. FIG. 2D: Comparison of T-antigen, monosialylated ST-antigen and T-antigen/monosialylated ST-antigen ratio (T/ST) between 40 healthy control plasma samples and 6 plasma samples from different CDG-II patients including two patients with COG7, one with COG4 and two with mixed CDG-I and CDG-II disease. Controls are shown in mixed color and shape, and the six patients shown as triangles. Dashed lines represent cutoffs to separate patients from the normal controls.

FIG. 6A. Human control and GNE myopathy plasma O-glycan species were released by β-elimination and permethylated before MALDI-TOF/TOF analysis. Measured m/z and % intensity compared to the internal standard (I.S.) raffinose of the major detected small O-glycan species are shown as well as their structures (squares, GalNAc; circles, Gal; diamonds, Neu5Ac; squares, GlcNAc). FIG. 6B. Comparison of concentrations of T-antigen, monosialylated T-antigen (ST) and their ratio T/ST in plasma (evaluated by LC-MS\MS) from 50 healthy controls (circles) and different GNE myopathy patients (squares). Plasma values of a GNE myopathy patient before (solid triangle) and after (open triangle) IVIG therapy are indicated. Dashed lines represent cutoffs to establish the normal range [~2× standard deviation (SD) of the mean (0.033)]. For additional information see Tables 5 and 6.

FIG. 7A. Immunoblotting with the NCAM RNL-1 antibody does not show an apparent different banding pattern in serum of GNE myopathy patients compared to control serum. Neuraminidase treated control serum did not show a different banding pattern. FIG. 7B-7C. Immunoblotting with the NCAM H-300 antibody (see also FIG. 4), showed a slight downshift of the 140 kDa NCAM isoform in serum of GNE myopathy patients compared to control serum. A similar downshift was present in neuraminidase treated control serum (NA). Dotted line is to aid in discerning migration.

FIG. 8A. Representative images of paraffin embedded muscle slides stained with each lectin as well as with substrate-inhibited lectin (green) and with the nuclear dye DAPI (blue). Each FITC-labeled lectin was incubated with its specific inhibitory carbohydrate (i.e., Neu5Ac for WGA and SNA, GalNAc for VVA) prior to incubation on muscle slides. Note that sugar-inhibited lectins (right panels) show a greatly reduced or absent fluorescent signal for each lectin compared to the original lectin signal (left panels). FIG. 8B. Representative images of paraffin embedded control muscle slides either untreated (−NA) or treated/desialylated with neuraminidase (+NA). Both the SNA and WGA signals greatly decreased after neuraminidase incubation, indicating de-sialylation of the tissue glycans and specificity of the lectins. A neuraminidase-inhibition control was not provided for VVA, since sialylated O-GalNAc (STn-antigen) is not present in normal muscle tissue (only in disease tissue).

FIG. 9A-9D. Western blotting followed by lectin staining of serum glycoproteins. Control (C-1, C-2), Neuraminidase treated control (NA), and GNE myopathy patients (GNE-2, -5, -10, -13, -16) serum was electrophoresed on SDS-PAGE gels, followed by electroblotting on nitrocellulose membranes. The membranes were incubated with the lectins WGA, SNA or VVA. 10 μg of total serum protein was loaded in the WGA and SNA labeled blots, and 20 μg total serum protein was loaded in the VVA labeled blot. The NA-treated control samples showed the expected reduction (for WGA and SNA) or increase (for VVA) in lectin binding, no significant differences in binding were present in GNE myopathy patients' compared to control samples. The Ponceau S stained membrane is an image from the blot before SNA labeling, and serves as a representative image for protein loading control of all blots (each blot was loaded with the same samples). The positive Ponceau S signal in the NA-treated lane and the absence of SNA staining in this lane, indicating total desialylation of NA-treated serum as well as specificity of the SNA lectin.

DETAILED DESCRIPTION OF SEVERAL EMBODIMENTS

Figure 1A:
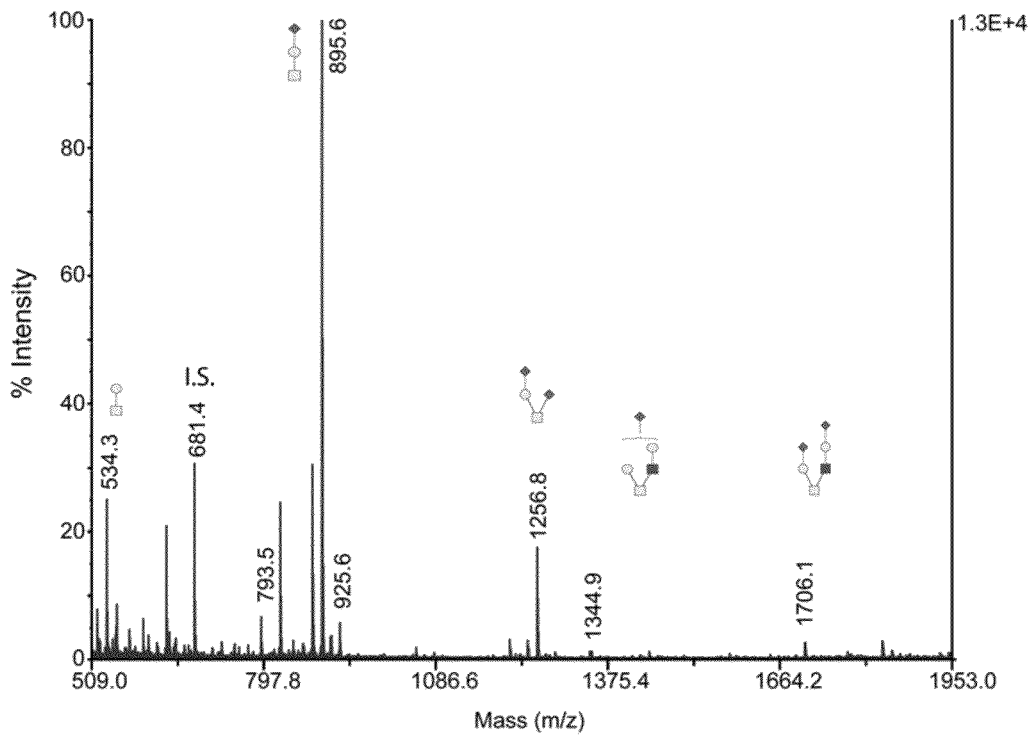
FIG. 1A-1B: Plasma O-glycan MALDI profile and quantitative comparison between 10 normal controls and 3 patients with Conserved Oligomeric Golgi (COG) deficiency.
Figure 1B:
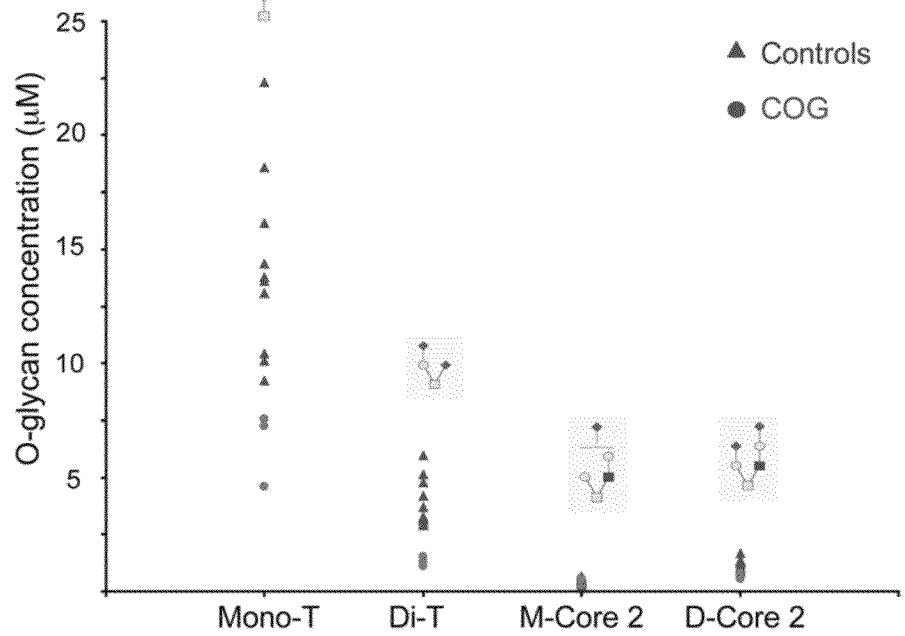

Methods are disclosed for diagnosing a hyposialylation disorder, including, but not limited to, a congenital disorder of glycosylation and GNE myopathy. Methods are also disclosed for determining the effectiveness of a therapeutic agent for treatment of a hyposialylation disorder in a subject. These methods include measuring an amount of monosialylated Thomsen-Friedenreich (ST) antigen, and measuring an amount of non-sialylated Thomsen-Friedenreich antigen (T) in a biological sample from the subject and determining the ratio of T to ST.

In additional embodiments, these methods can be used to determine the lowest effective dosage, or duration, of the therapeutic agent of use to treat the subject. The methods can be used to monitor the efficacy of a therapeutic agent.

TERMS

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). In order to facilitate review of the various embodiments of this disclosure, the following explanations of specific terms are provided:

Alteration: A statistically significant change in a parameter as compared to a control. In one example, an "increase" is a statistically significant elevation in a parameter, such as the presence of a biological marker, or the ratio of two biological markers, such at the T/ST ratio. The alternation can be measured as compared to a control. Suitable statistical analyses are well known in the art, and include, but are not limited to, Student's T test and ANOVA assays. In one example, a "decrease" or "reduction" is a statistically significant decline in a parameter, such as the presence of a biological marker, such as the T/ST ratio as compared to a control. In another example, an "increase" is a statistically significant higher level of a parameter, such as the presence of a biological marker, such as the T/ST ratio as compared to a control. Suitable statistical analyses are well known in the art, and include, but are not limited to, Student's T test and ANOVA assays.

Animal: Living multi-cellular vertebrate organisms, a category that includes, for example, mammals and birds. The term mammal includes both human and non-human mammals.

Congenital disorders of glycosylation (CDG): A group of disorders of abnormal glycosylation of glycans caused by deficiency one of the different steps in the synthetic, transport and metabolism pathways of glycans. Most commonly, the disorders begin in infancy; manifestations range from severe developmental delay and hypotonia with multiple organ system involvement to hypoglycemia and protein-losing enteropathy with normal development. However, most types have been described in only a few individuals, and thus understanding of the phenotypes is limited. In PMM2-CDG (CDG-Ia), the most common type reported, the clinical presentation and course are highly variable, ranging from death in infancy to mild involvement in adults.

CDG type I (CDG-I) disorders result from impaired synthesis of glycans, which may lead to unoccupied glycosylation sites on glycoproteins and glycolipids. CDG type II (CDG-II) includes defects in processing of glycans, which lead to accumulation of glycoproteins and glycolipids with abnormal structures. CDG-II includes defects in chaperones and Golgi-trafficking complexes, such as defects in the conserved oligomeric Golgi complex (COG), dolichol synthesis, and CMP-sialic acid synthesis, which impair multiple glycosylation pathways including both N- and O-glycan synthesis and N-glycan processing. Some multiple glycosylation defects may also present as mixed CDG-I and II. In addition, there is a growing number of patients with strong evidence of a glycosylation defect, whose molecular basis has not yet been identified (CDG-IIx).

Control: A value used as a source for comparison with an experimentally determined value. A control can be a standard value, a ratio (such as of a T/ST ratio) from one subject, or averaged from many subjects, who does not have a known disorder (such as a hyposialylation disorder), or a baseline concentration obtained from a subject at an earlier time point, prior to an onset of symptoms.

Determining or Measuring: Identifying the presence of a target molecule in a sample. There terms refer to measuring a quantity or quantitating a target molecule in the sample, either absolutely or relatively. For example, T and ST can be analyzed in a sample from a subject of interest, such as a subject suspected of having a hyposialylation disorder. The sample can be any biological sample of interest, such as, but not limited to, a plasma sample, serum sample, or tissue extract. Generally, detecting, measuring or determining a biological molecule requires performing an assay, such as mass spectrometry, and not simple observation.

Diagnosing or diagnosis of a hyposialylation disorder: Detecting the disorder by measuring specific parameters. For example, a hyposialylation disorder can be detected by determining the T/ST ratio in a biological sample. Diagnosis can encompass laboratory confirmation of a pre-existing clinical condition or a specific disease.

Glycoprotein: Proteins that contain oligosaccharide chains (glycans) covalently attached to polypeptide side-chains. The carbohydrate is attached to the protein in a cotranslational or posttranslational modification process known as glycosylation. There are two main types of glycosylation, N-glycosylation and O-glycosylation. In N-glycosylation, the addition of the sugar to a (protein) structure occurs on an amide nitrogen, such as in the side chain of an asparagine amino acid. In O-glycosylation, the addition of the sugar to a (protein) structure occurs on a hydroxyloxygen, such as on the side chain of hydroxylysine, hydroxyproline, serine or threonine amino acids. The sugars commonly found in eukaryotic glycoproteins include, but are not limited to, β-D-glucose, β-D-galactose, β-D-mannose, α-L-fucose, N-Acetylgalactosamine, N-Acetylglucosamine, N-Acetylneuraminic acid, and xylose.

Hereditary Inclusion Body Myopathy: A rare autosomal recessive neuromuscular disorder, also called GNE myopathy (and DMRV, Nonaka myopathy, IBM2 QIBM). (Argov, et al., *Neurology* 60, 1519-1523 (2003); Eisenberg, et al. (2001) *Nat Genet.* 29, 83-87 (2001); Griggs, et al. (1995) *Ann Neurol* 38, 705-713 (1995)) that is a hyosialylation disorder. The disease usually manifests after 20 years of age with foot drop and slowly progressive muscle weakness and atrophy. The cranial nerves, sensation, and mental acuity are all normal, and creatine kinase can be normal. Histologically, it is associated with muscle fiber degeneration and formation of vacuoles containing tubulofilaments that immunoreact like β-amyloid, ubiquitin, prion protein and other amyloid-related proteins (see Askanas et al. *Curr Opin Rheumatol* 10, 530-542 (1998); Nishino, et al. *Acta Myol* 24, 80-83 (2005); Askanas et al. *Ann Neurol* 34, 551-560 (1993); Argov et al. *Curr Opin Rheumatol* 10, 543-547 (1998)). Both weakness and histological changes initially spare the quadriceps. However, the disease is relentlessly progressive, with patients becoming incapacitated and wheelchair-confined within two to three decades. GNE myopathy is caused by mutations in the GNE gene, encoding the bifunctional key enzyme in sialic acid synthesis, UDP-N-acetylglucosamine-2-epimerase/N-acetylmannosamine kinase. Human GNE mutations result in lower activities of both epimerase and kinase function of this enzyme. The decrease or absence of these GNE enzymatic activities results in decreased de novo production of sialic acid, causing hyposialylation of glycoprotein and glycolipids, specifically a decrease in sialylation of O-linked glycans. In GNE myopathy, hyposialylation is found mainly on O-linked glycans in muscle. (See, for example, Huizing and Krasnewich, *Biochim Biophys Acta* 1792, 881-887 (2002); Huizing et al. GNE myopathy. *Scriver's Online Metabolic and Molecular Bases of Inherited Disease.* avilable at ommbid.com (258), (2013)).

Hyposialylation: Reduced or absent addition of sialic acid (N-acetyl neuraminic acid (Neu5Ac) and its derivatives) to galactose (Gal) or other underlying monosaccharides (such as, but not limited to N-acetylgalactose (GalNAc)), Mannose (Man), N-acetylglucosamine (GlcNAc), N-acetylneuraminic acid (Neu5Ac) or of sialic acid chains in polysialylation (PSA), such as on PSA-NCAM.

Hyposialylation disorders are conditions with hyposialylation of glycoproteins and glycolipids in affected tissues. Hyposialylation of affected tissues can be detected, for example, using histochemistry staining of fixed tissue slides with specific lectins. A demonstration of a significant reduction (or absence) of sialic acid, either by a statistically reduced staining/binding of sialic acid recognizing lectins (such as, but not limited to wheat germ agglutinin (WGA), *Sambucus nigra* agglutinin (SNA), and *Limax flavus* agglutinin (LFA) or by presence of staining of free monosaccharides underlying sialic acid on the glycan chain, including galactose or GalNAc, by the lectins (such as, but not limited to, *helix pomatia* agglutinin (HPA), *Vicia villosa* agglutinin (VVA), jackfruit agglutinin (Jacalin), and peanut agglutinin (PNA) can be used to identify hyposialylation disorders, such as certain cases with myopathy (including the adult-onset, progressive, autosomal recessive muscular disorder, GNE myopathy, also called distal myopathy with rimmed vacuoles (DMRV)/hereditary inclusion body myopathy (HIBM)), renal disorders (including, but not limited to minimal change nephrosis, lupus nephritis, IgA nephropathy), sleep disorders (including those with reduced REM sleep), neurodegenerative disorders (including those with amyloid depositions), cancers and liver disorders. Hyposialylation disorders include congenital disorders of glycosylation. Western blotting or 2D gel electrophoresis followed by lectin labeling or immunolabeling with a specific antibody to a sialoglycan can be used to detect hyposialylation disorders (these methods are exemplary only and are not limiting). Methods for detecting are disclosed, for example, in Kakani et al. *Am J Pathol* 180, 1431-1440 (2012); Niethamer et al. *Mol Genet Metab* 107, 748-755 (2012).

Intravenous Immunoglobulin (IVIG): A blood product that includes pooled polyvalent IgG extract from the plasma of a number of blood donors. It is used as treatment for immune deficiencies such as X-linked agammaglobulinemia, autoimmune diseases, such as immune thrombocytopenia and Kawaski disease, and acute infections.

Ion Exchange Chromatography: A chromatographic process that allows the separation of ions and polar molecules based on their charge. Ion-exchange chromatography retains analyte molecules on the column based on coulombic (ionic) interactions. The stationary phase surface displays ionic functional groups (R-X) that interact with analyte ions of opposite charge. This type of chromatography is further subdivided into cation exchange chromatography and anion exchange chromatography. The ionic compound consisting of the cationic species M+ and the anionic species B− can be retained by the stationary phase.

Generally, a sample is introduced, either manually or with an autosampler, into a sample loop of known volume. A buffered aqueous solution (often called the "mobile phase") carries the sample from the loop onto a column that contains a stationary phase material that is typically a resin or gel matrix consisting of agarose or cellulose beads with covalently bonded charged functional groups. The target analytes (either anions or cations) are retained on the stationary phase, but can be eluted by increasing the concentration of a similarly charged species that will displace the analyte ions from the stationary phase. For example, in cation exchange chromatography, the positively charged analyte can be displaced by the addition of positively charged sodium ions. The analytes of interest are detected, such as by conductivity or an ultraviolet (UV)/Visible light absorbance. Generally, a chromatography data system (CDS) is used to control the chromatography system.

Mass Spectrometry: A process used to separate and identify molecules based on their mass. Mass spectrometry ionizes chemical compounds to generate charged molecules or molecule fragments and measures their mass-to-charge ratios. In a typical MS procedure, as sample is ionized. The ions are separated according to their mass-to-charge ratio, and the ions are dynamically detected by some mechanism capable of detecting energetic charged particles. The signal is processed into the spectra of the masses of the particles of that sample. The elements or molecules are identified by correlating known masses by the identified masses. "Time-of-flight mass spectrometry" (TOFMS) is a method of mass spectrometry in which an ion's mass-to-charge ratio is determined via a time measurement. Ions are accelerated by an electric field of known strength. This acceleration results in an ion having the same kinetic energy as any other ion that has the same charge. The velocity of the ion depends on the mass-to-charge ratio. The time that it subsequently takes for the particle to reach a detector at a known distance is measured. This time will depend on the mass-to-charge ratio of the particle (heavier particles reach lower speeds). From this time and the known experimental parameters one can find the mass-to-charge ratio of the ion. "Liquid chromatography-mass spectrometry" or "LC-MS" is a chemistry technique that combines the physical separation capabilities of liquid chromatography (or HPLC) with the mass analysis capabilities of mass spectrometry. Liquid chromatography mass spectrometry (LC-MS) separates compounds chromatographically before they are introduced to the ion source and mass spectrometer. It differs from gas chromatography (GC-MS) in that the mobile phase is liquid, usually a mixture of water and organic solvents, instead of gas and the ions fragments. Most commonly, an electrospray ionization source is used in LC-MS.

Mean and Standard Deviation: The arithmetic mean is the "standard" average, often simply called the "mean".

$$\bar{x} = \frac{1}{n} \cdot \sum_{i=1}^{n} x_i$$

The mean is the arithmetic average of a set of values.

The standard deviation (represented by the symbol sigma, σ) shows how much variation or "dispersion" exists from the mean. The standard deviation of a random variable, statistical population, data set, or probability distribution is the square root of its variance. The standard deviation is commonly used to measure confidence in statistical conclusions. Generally, twice the standard deviation is about the radius of a 95 percent confidence interval. Effects that fall far outside the range of standard deviation are generally considered statistically significant. One of skill in the art can readily calculate the mean and the standard deviation from a population of values.

N-acetyl-D-mannosamine: The structure of N-acetyl-mannosamine is.

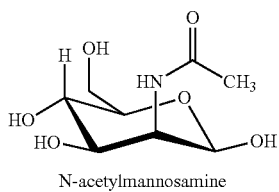

N-acetylmannosamine

N-acetylmannosamine and derivatives thereof can also be used. The structures of such N-acetylmannosamine derivatives useful in the invention are defined by Formula I.

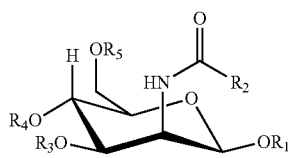

I wherein:

$R_1$, $R_3$, $R_4$, or $R_5$ is hydrogen, lower alkanoyl, carboxylate or lower alkyl; and $R_2$ is lower alkyl, lower alkanoylalkyl, lower alkyl alkanoyloxy. Derivates of N-acetylmanosamine are known; several exemplary derivatives are disclosed below.

Neurodegenerative disorder: A disease or condition associated with progressive loss of the structure or function of neurons. Neurodegenerative disorders include, but are not limited to Parkinson's disease, Alzheimer's disease and Huntington's disease.

Alzheimer's disease is the most common form of dementia. In the early stages, the most common symptom is difficulty in remembering recent events. When Alzheimer's disease is suspected, the diagnosis is usually confirmed with tests that evaluate behavior and thinking abilities, often followed by a brain scan. As the disease advances, symptoms can include confusion, irritability and aggression, mood swings, trouble with language, and long-term memory loss Alzheimer's disease is characterized by loss of neurons and synapses in the cerebral cortex and certain subcortical regions. This loss results in gross atrophy of the affected regions, including degeneration in the temporal lobe and parietal lobe, and parts of the frontal cortex and cingulate gyms. Both amyloid plaques and neurofibrillary tangles are clearly visible by microscopy in brains of those afflicted by Alzheimer's disease. Plaques are dense, mostly insoluble deposits of β-amyloid peptide and cellular material outside and around neurons. Tangles (neurofibrillary tangles) are aggregates of the microtubule-associated protein tau which has become hyperphosphorylated and accumulate inside the cells themselves. Although many older individuals develop some plaques and tangles as a consequence of ageing, the brains of people with Alzheimer's disease have a greater number of them in specific brain regions such as the temporal lobe Neurodegenerative diseases, such as, but not limited to, Alzheimer's disease, can be associated with accumulation of β-amyloid in the brain. β-amyloid is a polypeptide of 36-43 amino acids that is processed from the amyloid precursor protein that is the main component of deposits found in the brains of patients with Alzheimer's disease. Similar plaques appear in some variants of Lewy body dementia and in inclusion body myositis (a muscle disease), while β-amyloid can also form the aggregates that coat cerebral blood vessels in cerebral amyloid angiopathy. The plaques are composed of a tangle of regularly ordered fibrillar aggregates called amyloid fibers, a protein fold shared by other peptides such as the prions associated with protein misfolding diseases.

Amyloid also accumulates in muscle of patients with GNE myopathy. Without being bound by theory, hyposialylation of amyloid precursor protein (APP) has been proposed to be important in misfolding and accumulation of amyloid, a process that may occur in GNE myopathy muscle tissue and could be important in some neurodegenerative diseases with brain amyloid accumulation.

Purified: The term "purified" does not require absolute purity; rather, it is intended as a relative term. Thus, for example, a purified glycoprotein preparation is one in which the glycoprotein referred to is more pure than the protein in its natural environment within a cell. For example, a preparation of a glycoprotein is purified such that the glycoprotein represents at least 60%, 70%, 80%, 90%, 95%, 96%, 97%, 98%, or 99% of the total biomolecule content of the preparation.

Renal hyposialylation disorder: A disease of the kidneys characterized by decreased sialylation. In some subjects, the glomeruli are hyposialylated. These disorders include some forms of podocytopathies, minimal change nephrosis, focal and segmental glomerulosclerosis, membranous glomerulonephritis, and other forms of unexplained idiopathic nephrotic syndrome, as well as glomerular basement membrane diseases such as Alport disease and thin membrane disease. Such kidney disorders and conditions are sometimes characterized by segmental splitting of the glomerular basement membrane and/or podocytopathy due to disturbed polyanions on podocyte membranes, or to changes in the amount or charge (sialylation) of glomerular basement membrane components.

Sample: A biological specimen containing genomic DNA, RNA (including mRNA), protein, glycoprotein, or combinations thereof, obtained from a subject. In some examples, a sample is a bodily fluid, such as, but not limited to, a blood, serum, or plasma sample. A sample can be a cell or a tissue extract, such as, but not limited to, platelets, red blood cells, or liver, muscle or kidney biopsy (or cell) extracts. A bodily fluid is a natural liquid or secretion of a subject's body, including cerebrospinal fluid or urine.

Sialic acid: A negative charged sugar that is a terminal sugar on glycans. The most common sialic acid is 5-N-acetyl-neuraminic acid, a monosaccharide with a nine-carbon backbone. Other less common sialic acids are N- or O-substituted derivatives of 5-N-neuraminic acid. Sialic acids are found widely distributed in animal tissues and to a lesser extent in other species, ranging from plants and fungi to yeasts and bacteria, mostly in glycoproteins and gangliosides. The amino group generally bears either an acetyl or glycolyl group. The hydroxyl substituents include acetyl, lactyl, methyl, sulfate, and phosphate groups. Sialic acid is transferred to an oligosaccharide by a sialyltransferase.

In renal functions, sialic acid residues are important for maintenance of glomerular integrity, facilitating glomerular filtration, and their deficiency is implicated in proteinuria and/or hematuria. It has also been reported that glomerular podocyte and podocyte foot process morphologies are maintained by the anionic charge of sialic acid residues on podocyte glycoproteins and glycolipids, and that a barrier to protein permeability is controlled by functional endothelial glycocalyx, rich in sialic acid.

Sleep disorder: A medical disorder of the sleep patterns of a person or animal. Some sleep disorders are serious enough to interfere with normal physical, mental and emotional functioning. Polysomnography is a test commonly used to diagnose some sleep disorders. Sleep disorders include primary insomnia, bruxism, delayed sleep phase syndrome, hyopnea syndrome, nacrcolepsy, cataplexy, night tenors, parasomnia, periodic limb movement disorder (PLMD), rapid eye movement (REM) behavior disorders, restless leg syndrome, sleep apnea, sleep paralysis, sleepwalking, nocturia, or somniphobia. Sleep disorders associated with hyposialylation include sleep volume reductions and sleep quality reductions, the former manifesting themselves as increased sleep onset time, inadequate sleep time due to premature arousal and the like, and the latter developing as symptoms such as bedtime shifts, decreased deep sleep (non-REM sleep), sleep interruptions due to premature arousal, and naps in active time zones. Sleep disorders occur irrespective of the patient's age; especially the quality of sleep decreases with aging (see U.S. Published Patent Application No. 2011/0212917, incorporated herein by reference).

Diagnosis can be made by a test consisting of a plurality of inquiries, and is established by electroencephalography or by polysomnography, which measures multiple parameters, including electroencephalograms. Diagnoses can be classified according to internationally recognized criteria (The International Classification of Sleep Disorder, ICSD).

Rapid eye movement sleep behavior disorder (RBD) is a sleep disorder that involves abnormal behavior during the sleep phase with rapid eye movement (REM sleep). The major and abnormal feature of RBD is loss of muscle atonia (paralysis) during otherwise intact REM sleep. This is the stage of sleep in which most vivid dreaming occurs. The loss of motor inhibition leads to a wide spectrum of behavioral release during sleep. This extends from simple limb twitches to more complex integrated movement, in which sufferers appear to be unconsciously acting out their dreams. These behaviors can be violent in nature and in some cases will result in injury to either the patient or their bed partner. Sleep disorders are disclosed in U.S. Published Patent Application No. 2011/0212917, which is incorporated herein by reference.

Standard: A substance or solution of a substance of known amount, purity or concentration that is useful as a control. A standard can also be a known value or concentration of a particular substance. A standard can be compared (such as by spectrometric, chromatographic, spectrophotometric, or statistical analysis) to an unknown sample (of the same or similar substance) to determine the presence of the substance in the sample and/or determine the amount, purity or concentration of the unknown sample. In one embodiment, a standard is a particular T/ST ratio. In another embodiment, a standard is a known ratio of T/ST that is found in a sample from a subject that does not have a hyposialylation disorder.

Subject: Living organisms susceptible to a hyposialylation disorder; a category that includes both human and non-human mammals, such as non-human primates.

Figure 3:
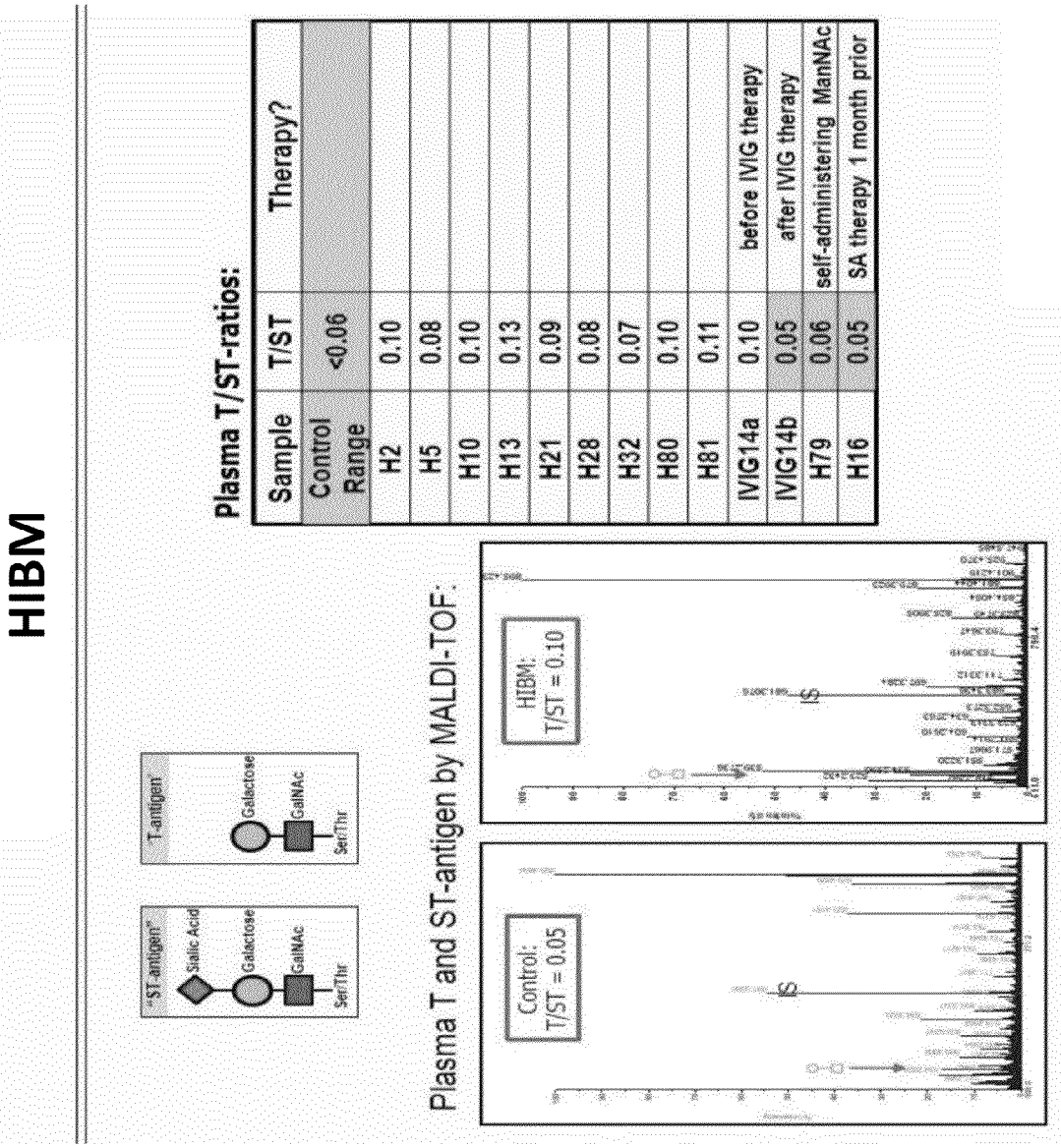
FIG. 3. T/monosialylated ST Ratio as a biomarker for HIBM/GNE myopathy. The structure of T and monosialylated ST are provided at the top. Exemplary MALDI-TOF analyses are shown in the left panels. A table of the ratios for a subset of patients is provided on the right of the figure.

Thomsen-Friedenreich Antigen: N-actetyl galactosamine linked Galactose (Gal-GalNAc), also known as "T" antigen. The monosialylated form of this antigen (Sialic Acid-Gal-GalNAc) is called "ST" antigen; a disialylated form also exists. The structures of T and ST are shown in FIG. 3.

Therapeutic agent: A molecule, such as a chemical compound, antibody, small molecule, nucleic acid, protein, oligosaccharide, or glycoprotein used for the treatment of a disorder.

Under conditions sufficient for: A phrase that is used to describe any environment that permits the desired activity.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Methods

Methods are disclosed herein for diagnosing a hyposialylation disorder, including confirming the diagnosis of a hypopsialylation disorder. These methods include obtaining a biological sample from a subject of interest, such as a subject suspected of having a hyposialylation disorder, measuring the amount of monosialylated Thomsen-Friedenreich (ST) antigen, and measuring the amount of non-sialylated Thomsen-Friedenreich antigen (T) in the biological sample. The ratio of T to ST (T/ST) in the biological sample is determined.

In some embodiments, a method is provided for diagnosing a hyposialylation disorder, for example confirming the diagnosis of a hyposialylation disorder, that includes quantitating the amount of monosialylated Thomsen-Friedenreich (ST) antigen in a biological sample from the subject and quantitating the amount of non-sialylated Thomsen-Friedenreich antigen (T) in the biological sample from the subject. The ratio of T to ST is determined. The ratio of T to ST can be compared to a control, such as a standard value.

In some embodiments, a ratio of T to monosialylated ST (T/ST) in a plasma or serum sample of greater than about 0.051 to greater than about 0.062, greater than about 0.052 to greater than about 0.06, greater than about 0.058 to greater than about 0.062, such as about 0.052 or greater, about 0.053 or greater, about 0.054 or greater, about 0.055 or greater, about 0.056 or greater, about 0.057 or greater, about 0.058 or greater, about 0.059 or greater, or about 0.06 or greater indicates that the overall sialylation of O-linked glycoproteins in the plasma or serum is below 95% of the population and that the subject has the hyposialylation disorder, or confirms the diagnosis of the hyposialylation disorder. In some embodiments, a T/ST ratio in serum or plasma of greater than about 0.07, about 0.08, about 0.09, or about 0.1 indicates that the subject has a hyposialylation disorder. In other embodiments, a ratio of T to ST (T/ST) of less than about 0.06, less than about 0.059, less than about 0.058, less than about 0.057, less than about 0.056, less than about 0.054, less than about 0.053, less than about 0.052, or less than about 0.051, in plasma or serum indicates that the subject does not have the hyposialylation disorder. In some embodiments, a ratio of T to ST in plasma or serum of less than about 0.05, about 0.04 or about 0.03 indicates that the subject does not have a hyposialylation disorder. In this context, "about" indicates within about 0.005.

In some specific non-limiting examples, the biological sample is a serum or plasma sample. Exemplary results showing the establishment of the about 0.06 cutoff value for patients with a hyposialylation disorder, and validation with patients plasma samples are provided in FIG. 2D and FIG. 6B. Exemplary results showing the establishment of the about 0.052 cut off value for patients without a hyposialylation disorder, and a cut off value of 0.06 for patients with a hyposialylation disorder, is also provided in FIG. 6B.

In some embodiments, the methods also include administering to the subject a therapeutic agent for the treatment of the hyposialylation disorder, such as if the T to ST in a serum or plasma sample from the subject is greater than about 0.051 to greater than about 0.062, greater than about 0.052 to greater than about 0.06, greater than about 0.058 to greater than about 0.062, such as about 0.052 or greater, about 0.053 or greater, about 0.054 or greater, about 0.055 or greater, about 0.056 or greater, about 0.057 or greater, about 0.058 or greater, about 0.059 or greater, or about 0.06 or greater. Suitable therapeutic agents are disclosed below.

A ratio of T to monosialylated ST (T/ST) can also be measured in biological samples other than serum or plasma, including, but not limited to platelets, red cells, white cells, cerebrospinal fluid, urine or a biopsy sample, such as a liver biopsy, muscle biopsy or kidney biopsy. In some embodiments, T and monosialylated ST are measured in biological samples from subjects known not to have the hyposialylation disorder, and a control ratio of the T to ST is established. T and ST are measured in a biological sample from a subject of interest, to determine if the subject has the hyposialylation disorder. In some embodiments, a T to ST ratio of greater than two standard deviations greater than the control ratio of T to ST diagnoses the hyposialylation disorder. In additional embodiments, a ratio of T to ST of greater than three standard deviations than the control ratio of T to ST diagnoses the hyposialylation disorder. In some embodiments, the methods also include administering to the subject a therapeutic agent for the treatment of the hyposialylation disorder, such as if the T to ST in a tissue sample other than serum or plasma is greater than two standard deviations, such as three standard deviations greater than the ratio of T to ST for the control, such as the mean T/ST ratio for biological samples from subjects without the hyposialylation disorder (and/or without any sialylation disorder). Suitable therapeutic agents are disclosed below.

Methods are also disclosed herein for determining the effectiveness of a first dosage, or the duration of a dosage, of a therapeutic agent for treatment of a hyposialylation disorder in a subject. The method can determine if a therapeutic agent of interest is of use for treating the hyposialylation disorder in a subject, or if the therapeutic agent has been administered for a sufficient period of time to treat the subject. The methods can be used to determine the lowest effective therapeutic dosage of an agent for the treatment of a subject. These methods include measuring monosialylated ST antigen and T antigen in a biological sample from the subject administered the therapeutic agent. The method can include quantitating the amount of monosialylated ST antigen and quantitating the amount of T antigen in a biological sample from the subject administered the therapeutic agent. In some embodiments, the methods include administering the therapeutic agent to the subject. The ratio of T to monosialylated ST is determined.

In some embodiments, a ratio of T to ST in a plasma or serum sample of less than about 0.06, less than about 0.059, less than about 0.058, less than about 0.057, less than about 0.056, less than about 0.054, less than about 0.053, less than about 0.052, or less than about 0.051 indicates that the first dosage of the therapeutic agent is effective for the treatment of the hyposialylation disorder, and/or that the therapeutic agent has been administered for a sufficient duration of time to treat the subject. In additional embodiments, a ratio of T to ST of less than about 0.05, about 0.04 or about 0.03 indicates that the first dosage of the therapeutic agent is effective for the treatment of the hyposialylation disorder, and/or that the therapeutic agent has been administered for a sufficient duration of time to treat the subject.

In additional embodiments, a ratio of T to ST of greater than about 0.051, greater than about 0.052, greater than about 0.053, greater than about 0.054, greater than about 0.055, greater than about 0.056, greater than about 0.057 or greater, greater than about 0.058, greater than about 0.059, or greater than about 0.06, such as in serum or plasma, indicates that the first dosage of the therapeutic agent is not effective for the treatment of the hyposialylation disorder and/or that the therapeutic agent has not been administered for a sufficient duration of time to treat the subject. In some embodiments, a serum or plasma T/ST ratio of greater than about 0.07, about 0.08, about 0.09, or about 0.1 indicates that the first dosage of the therapeutic agent is not effective for treating the subject, and/or that the therapeutic agent has not been administered for a sufficient duration of time to treat the subject.

In some non-limiting examples, for any of the methods disclosed herein, the biological sample can be a sample other than serum or plasma. In some embodiments, a ratio of T to monosialylated ST of at least two standard deviations less than a control ratio of T to ST indicates that the first dosage of the therapeutic agent is effective for the treatment of the hyposialylation disorder and/or that the therapeutic agent has not been administered for a sufficient duration of time to treat the subject. In yet other embodiments, a ratio of T to monosialylated ST of at least three standard deviations less than a control ratio of T to ST for a control indicates that the first dosage of the therapeutic agent is effective for the treatment of the hyposialylation disorder and/or that the therapeutic agent has been administered for a sufficient duration of time to treat the subject. In further embodiments, the control ratio is the mean ratio of T to ST in biological samples from subjects that do not have the hyposialylation disorder. The biological sample can be any biological sample of interest, such as blood, an extract from a biopsy, such as an extract of platelets, white blood cell, red blood cells, kidney cells, muscle cells, heart cells, brain cells, lung cells, or liver cells. The biological sample can be urine or cerebrospinal fluid.

In certain aspects, these assays are performed at a diagnostic laboratory, and the information is then provided to the subject or a physician or other healthcare provider. In some embodiments, the dosage of the therapeutic agent is decreased, and a second lower dosage of the therapeutic agent is administered to the subject. In additional embodiments, these methods can be used to determine the lowest effective dosage of the therapeutic agent of use to treat the subject. In yet other embodiments, the dosage of the therapeutic is increased and administered to the subject. In other examples, and additional dosage of the therapeutic agent is administered to the subject.

Thus, in additional embodiments, the method can include administering to the subject a second dosage of the therapeutic agent, wherein the second dosage is the same, greater, or less than the first dosage of the therapeutic agent. Monosialylated ST antigen and T antigen are measured in a biological sample from the subject, and the ratio of T to ST is determined.

In some embodiments, a ratio of T to monosialylated ST in serum or plasma samples of less than about 0.0521, less than about 0.052, less than about 0.053, less than about 0.054, less than about 0.055, less than about 0.056, less than about 0.057, less than about 0.058, less than about 0.059, or less than about 0.06, indicates that the second dosage of the therapeutic agent is effective for the treatment of the hyposialylation disorder and/or has been administered for a sufficient duration. In some embodiments, a ratio of T to ST of less than about 0.05, about 0.04 or about 0.03 in the plasma or serum sample indicates that the second dosage of the therapeutic agent is effective for the treatment of the hyposialylation disorder and/or has been administered for a sufficient duration. A ratio of T to ST of greater than about 0.051, greater than about 0.052, greater than about 0.053, greater than about 0.054, greater than about 0.055, greater than about 0.056, greater than about 0.057 or greater, greater than about 0.058, greater than about 0.059, or greater than about 0.06 in the plasma or serum sample indicates that the second dosage of the therapeutic agent is not effective for the treatment of the hyposialylation disorder and/or has not been administered for a sufficient duration. In other embodiments, a ratio of T to ST of greater than about 07, about 0.08, about 0.09, or about 0.1 in the plasma or the serum sample indicates that the second dosage of the therapeutic agent is not effective for the treatment of the hyposialylation disorder. Thus, in some embodiments, the methods disclosed herein can be repeated to determine the lowest dosage of an agent that is effective for the treatment of the subject.

In some embodiments, in other samples than plasma or serum, a ratio of T to monosialylated ST of at least two standard deviations less than a control ratio of T to ST for a control indicates that the second dosage of the therapeutic agent is effective for the treatment of the hyposialylation disorder and/or is administered for a sufficient duration to treat the subject. In yet other embodiments, a ratio of T to monosialylated ST of at least three standard deviations less than a control ratio of T to monosialylated ST for a control indicates that the second dosage of the therapeutic agent is effective for the treatment of the hyposialylation disorder and/or that the therapeutic agent has been administered for a sufficient duration of time to treat the subject. In further embodiments, the control ratio is the mean ratio of T to monosialylated ST in biological samples from subjects that do not have the hyposialylation disorder. Thus, the methods can be repeated to determine the lowest dosage of an agent that is effective for the treatment of the subject. The biological sample can be any biological sample of interest, such as an extract from a tissue biopsy, such as an extract of platelets, white blood cell, red blood cells, kidney cells, muscle cells, heart cells, brain cells, lung cells, or liver cells. The biological sample can be blood, urine or cerebrospinal fluid.

The methods can be repeated 1, 2, 3, 4, 5, 6, 7, 8, 9, 10 or more times to determine the lowest dosage of a therapeutic agent that is effective for treating the subject, and/or the shortest duration of administration that is effective for treating the subject. The methods can also be used over the course of a therapeutic regimen to monitor the efficacy of a therapeutic agent for the treatment of the subject.

The disclosed methods can include comparing the ratio of T to monosialylated ST to a control. The control can be a standard value, or the ratio of T to monosialylated ST in a biological sample from a subject known not to have the sialylation disorder, such as the hyposialylation disorder.

The hyposialylation disorder can be any hyposialylation disorder of interest. In other non-limiting examples, the hyposialylation disorder is a congenital disorder of glycosylation, such as an N-linked glycosylation disorder, O-linked glycosylation disorder, multiple glycosylation disorder or disorder of glycolipid synthesis, or CDGII. In other specific non-limiting examples, the hyposialylation disorder is not a congenital disorder of glycosylation, such as a CDGII. Hyposialylation disorders include, but are not limited to hereditary inclusion body myopathy, also called GNE myopathy or distal myopathy with rimmed vacuoles (DMRV). In some embodiments, the hyposialylation disorder can include renal hyposialylation. These include, but are not limited to, minimal change nephrosis, lupus nephritis, and IgA nephropathy. In other embodiments, the hyposialylation disorder is a sleep disorder, including those with reduced REM sleep, or a disorder due to brain hypofunction, see U.S. Published Patent Application No. 2011/0212917, incorporated herein by reference. In additional embodiments, the hyposialylation disorder is a neurodegenerative disorder, such as a disorder that includes accumulation of β-amyloid, such as Alzheimer's disease and Lewy body dementia. In additional examples, the neurodegenerative disorder is a cognitive disorder involving brain hypofunction. In other embodiments, the hyposialylation disorder is a liver disorder, or a muscular disorder. In some specific, non-limiting examples, the hyposialylation disorder is a congenital muscular dystrophy or inclusion body myositis. The hyposialylation disorder can be a cancer. In further embodiment, the hyposialylation disorder is a kidney or a liver disorder, such as podocytopathies, minimal change nephrosis, focal and segmental glomerulosclerosis, membranous glomerulonephritis, and other forms of unexplained idiopathic nephrotic syndrome, glomerular basement membrane diseases (such as Alport disease and thin membrane disease). In some examples, the kidney disorder is characterized by segmental splitting of the glomerular basement membrane and/or podocytopathy due to disturbed polyanions on podocyte membranes.

The method can include purifying O-glycans from the biological sample. Thus, the method can include releasing O-glycans, such as by treating the biological sample with sodium hydroxide and sodium borohydrate. Suitable concentrations of sodium hydroxide and sodium borohydrate are, for example, about 1M sodium borohydrate in 0.05M sodium hydroxide. In some embodiments, O-glycans are purified from the biological sample. Methods for purifying O-glycans include organic solvent extraction with methanol, and ion-exchange chromatography, such as with AG 50W-X8 resin (Bio-Rad, Hercules, Calif.). Exemplary non-limiting methods are disclosed in the examples section.

Disclosed herein are methods of detecting biomarkers for hyposialylation disorders in order to detect the hyposialylation disorder or to determine if a therapeutic agent is effective for the treatment of this disorder, and methods for detecting a hyposialylation disorder. The monosialylated ST antigen and T antigen biomarkers may be detected using any means known to those of skill in the art, including the use of antibodies that specifically bind T antigen, antibodies that specifically bind ST antigen (see, for example, Cao et al., Histochemistry and Cell Biol. 106(2): 197-207, 1996), and/or the use of lectins that bind T and/or ST antigen, see for example, Almogren et al., Frontiers in Bioscience S4: 840-863, 2012, incorporated herein by reference. These methods include fluorescence activated cell sorting (FACS), enzyme linked immunosorbant assays (ELISA), Western blotting and 2D gelelectrophoresis. Generally, the monosialylated ST antigen and T antigen biomarkers are quantitated.

In particular disclosed embodiments of the method, the biomarkers are detected as a ratio using mass spectrometry. Any mass spectrometry technique known to those of ordinary skill in the art to be suitable for analyzing biological molecules can be utilized. For example, mass spectrometric techniques contemplated herein include mass spectrometry techniques using various ionization techniques (such as, but not limited to, matrix-assisted laser desorption/ionization (MALDI), electrospray, thermospray, and the like) coupled with one or more mass analyzer components (such as, but not limited to, time-of-flight [TOF], quadrupole, and ion traps). Any of the mass spectrometry detection methods used herein may also be modified to perform tandem mass spectrometry, and/or may be modified to employ additional analytical techniques, such as liquid chromatography, gas chromatography, and ion mobility.

Mass spectrometry has been used as a powerful tool to characterize polymers such as glycans because of its accuracy (.+-.1 Dalton) in reporting the masses of fragments generated (e.g., by enzymatic cleavage), and also because only pM sample concentrations are required. For example, matrix-assisted laser desorption ionization mass spectrometry (MALDI-MS) has been described for identifying the molecular weight of polysaccharide fragments in publications such as Rhomberg, et al., PNAS USA 95, 4176-4181 (1998); Rhomberg, et al., PNAS USA 95, 12232-12237 (1998); and Ernst, et al. PNAS USA 95, 4182-4187 (1998). Other types of mass spectrometry known the art, such as electron spray-MS, fast atom bombardment mass spectrometry (FAB-MS) and collision-activated dissociation mass spectrometry (CAD) can also be used. However, the disclosed methods are not limited to the use of mass spectrometry. Other methods of use include, but are not limited to, capillary electrophoresis (CE), NMR, and HPLC with fluorescence detection.

The techniques, including mass spectrometry techniques disclosed herein may be used to determine the ratio of biomarkers present in a biological sample. For example, particular embodiments concern the core1 monosialylated ST antigen and the T antigen. The ratio of these two antigens within a particular biological sample may be determined by using the disclosed mass spectrometry techniques to produce one or more ions identifying the particular antigen. For example, a sample may be added to a mass spectrometer, which promotes fragmentation of the components within the sample to produce various different ions associated with each component.

Multiple reaction monitoring may be used to produce a unique fragment ion that can be monitored and quantified. In particular disclosed embodiments, the parent mass of the compound is specified and the sample comprising the compound is monitored for the unique fragment ion. Typically, the parent mass/ion of the compound is selected and fragmented and either a particular fragment, the unique fragment ion, is analyzed or all fragments from the parent ion are analyzed. The ratio of each compound can be determined using quantitative mass spectrometry, such as by using an internal standard. In particular disclosed embodiments, the monosialylated ST and T antigen have different mass transitions, which can be determined in order to quantify the ratio of the two antigens in a biological sample. Typically, the monosialylated ST antigen will have a parent mass (or parent ion m/z) of 895 and the fragment ion is 520. The T antigen can have a parent mass (or parent ion m/z) of 534 and the fragment ion is 298. The concentration of each of the monosialylated antigen and the T antigen can be measured by comparing the signals from the internal standard with that produced by either the ST or T antigens. In particular disclosed embodiments, one or more calibration curves may be produced using various different concentrations of either antigen.

According to one embodiment of the disclosed methods, a biological sample (e.g., a blood sample, plasma sample, tissue extract etc.) is collected and prepared for analysis. As an example, an internal standard may be added to the biological sample in solution (e.g., aqueous solution). The biological sample may then be treated with a buffered base solution (e.g., an aqueous solution of sodium borate and sodium hydroxide) in order to promote denaturation of the serum proteins. The solution may be neutralized using an appropriate neutralizing solution (e.g., acetic acid in methanol), and the desired glycans extracted using methanol. The extracted glycans may be desalted using an ion exchange resin and then dried.

Once the desired biological sample is obtained, it may be manipulated in order to promote analysis using the disclosed mass spectrometric method. In particular disclosed embodiments, desalted glycans may be permethylated using a base and appropriate methylating agent. Solely by way of example, the glycan may be exposed to an aqueous solution of sodium hydroxide in dimethylsulfoxide (DMSO) and then treated with methyl iodide. After extraction, the permethylated glycans are purified, such as by a SPE C18 column, and used in the disclosed mass spectrometric analysis.

According to one embodiment, the permethylated glycans are analyzed using tandem mass spectrometry coupled with high-performance liquid chromatography (HPLC-MS/MS);

however, any suitable mass spectrometric methods may be used as disclosed herein. In particular disclosed embodiments, a suitable buffer/solvent system is selected for the HPLC analysis portion of the analytical technique. For example, a two-buffer system may be used. Particular disclosed embodiments concern using a first buffer of acetonitrile/formic acid/water having ratios of 1:0/1:99 (v:v:v), respectively, and a second buffer of acetonitrile/formic acid/water having ratios of 99:0/1:1 (v:v:v), respectively. Exemplary flow rate protocols are provided herein. In particular disclosed embodiments, mass spectrometry analysis is conducted using an enhanced product ion source in the positive mode and one or more quadrupole mass analyzers. Exemplary non-limiting methods are disclosed in the Examples section below.

Exemplary Therapeutic Agents

Methods are disclosed herein for determining the effectiveness of a therapeutic agent for treatment of a hyposialylation disorder in a subject, and/or that include administering a therapeutic agent to a subject. The therapeutic agent can be any agent of interest, including, but not limited to, N-acetyl-D-mannosamine (ManNAc), N-acetylneuraminic acid (Neu5Ac), sialic acid, or one or more sialylated compound. The one or more sialylated compounds can be the one or more sialylated compound can include intravenous immunoglobulin (IVIG) or sialyllactose.

The structure of N-acetylneuraminic acid (Neu5Ac) is shown below.

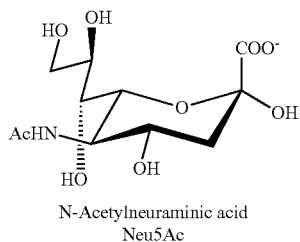

N-Acetylneuraminic acid
Neu5Ac

Intravenous immunoglobulin is pooled, polyvalent immunoglobulin G (IgG) extracted from donors. In some embodiments, IVIG is administered at a high dosage, such as about 100 to 400 mg per kg of body weight, or about 1 to about 2 grams IVIG per kg body weight.

N N-acetyl-mannosamine and derivatives thereof are useful for treating a variety of diseases and conditions, see for example, U.S. Published Patent Application No. 2013/0058998-A1, and U.S. Pat. No. 8,410,063, both incorporated herein by reference. N-acetyl-D-mannosamine is an uncharged, key compound in the sialic acid biosynthetic pathway, such as in the Neu5Ac biosynthetic pathway. Neu5Ac is the most abundant mammalian sialic acid, and precursor of most other sialic acids. In particular, there is a regulated, rate-limiting enzymatic step in the pathway that leads to silaic acid (e.g., Neu5Ac) formation, and this rate-limiting step gives rise to N-acetyl-D-mannosamine. Once N-acetyl-D-mannosamine is formed or administered, no other enzymatic step leading to the formation of Neu5Ac is subject to feedback inhibition. Administration of N-acetyl-D-mannosamine leads to increased amounts of neu5Ac. The structure of N-acetyl-mannosamine is shown below.

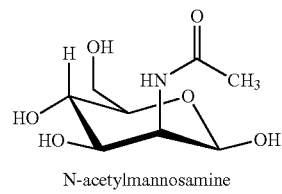

N-acetylmannosamine

N-acetylmannosamine and derivatives thereof can also be used for the treatment of hyposialylation disorders. Structures of such N-acetylmannosamine derivatives are provided in Formula I.

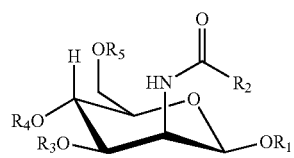

wherein:
$R_1$, $R_3$, $R_4$, or $R_5$ is hydrogen, lower alkanoyl, carboxylate or lower alkyl; and
$R_2$ is lower alkyl, lower alkanoylalkyl, lower alkyl alkanoyloxy.

Alkyl, alkoxy, alkenyl, and alkynyl denote both straight and branched groups; but reference to an individual radical such as "propyl" embraces only the straight chain radical, a branched chain isomer such as "isopropyl" being specifically referred to. Lower alkyl refers to $(C_1-C_6)$alkyl. Such a lower alkyl or $(C_1-C_6)$alkyl can be methyl, ethyl, propyl, isopropyl, butyl, iso-butyl, sec-butyl, pentyl, 3-pentyl, or hexyl; $(C_3-C_6)$ cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; ($C_2$-$C_6$)alkanoyloxy can be acetoxy, propanoyloxy, butanoyloxy, isobutanoyloxy, pentanoyloxy, or hexanoyloxy.

Administration of N-acetyl mannosamine and/or derivatives thereof can lead to a reduction in proteinuria (e.g., lower amounts of protein in the urine), a reduction in hematuria (e.g., lower amounts of red blood cells in the urine) and improvement of muscle function (e.g., in patients with muscular atrophy). Effective amounts for human patients are, for example, about 0.01 g/day to about 50 g/day, about 0.1 g/day to about 50 g/day, of about 0.2 g/day to about 25 g/day, from about 0.3 g/day to about 12 g/day, from about 0.4 g/day to about 10 g/day, from about 0.5 g/day to about 8 g/day, and from about 0.7 g/day to about 6 g/day. N-acetylmannosamine and/or derivatives thereof may be administered as single or divided dosages, for example, of at least about 0.01 mg/kg to about 500 to 750 mg/kg, of at least about 0.01 mg/kg to about 300 to 500 mg/kg, at least about 0.1 mg/kg to about 200 to 400 mg/kg or at least about 1 mg/kg to about 25 to 200 mg/kg of body weight, although other dosages may provide beneficial results. Generally, N-acetylmannosamine and/or a derivative thereof is administered for periods of time sufficient to increase the amount of sialic acid (e.g., Neu5Ac) in the mammal and thereby achieve a therapeutic benefit. The use of N-acetylmannosamine is disclosed in PCT Publication No. WO 2008/150477, which is incorporated herein by reference.

Exemplary components of the sialic acid biosynthesis pathway can be used as therapeutic agents, and include mannosamine, N-acetyl mannosamine (ManNAc) (see above), ManNAc-6-phosphate (ManNAc-6-P), UDP-GlcNAc, N-acetylneuraminic acid (Neu5Ac), NeuAc-9-phosphate (NeuAc-9-P), sialic acid (i.e., 5-N-acetylneuraminic acid and derivatives), and CMP-Neu5Ac acid. Hence, certain treatments include the direct administration of one or more of these components as compounds, or as derivatives or pharmaceutically acceptable salts thereof, including extended release formulations of such compounds (see, e.g., PCT Application No. PCT/US2011/043910, and U.S. Published Patent Application No. 2013/0058998A1, each of which is incorporated by reference in its entirety) or encapsulated compounds. In some examples, these compounds can be formulated for release over a defined time period such as 12, 24, 48, or 72 hours. The term "derivative" encompasses derivatives, analogs, prodrugs, and unnatural precursors of a given compound. In specific embodiments, the compound in the sialic acid (e.g., Neu5Ac) biosynthesis pathway or a derivative thereof does not include glucose or a pharmaceutically acceptable salt thereof.

Therapy with nucleic acid can also be utilized. Any gene involved in the sialic acid biosynthesis pathway, such as in the Neu5Ac biosynthesis pathway, can be utilized. In some embodiments, methods for increasing sialic acid production by providing a subject with a wild-type GNE-encoding nucleic acid sequence that is optionally operably linked to a regulatory element, such as a promoter and/or enhancer sequence (see U.S. Application No. 2011/027373; WO 2008/097623; and U.S. Application No. 2009/029811, which are incorporated by reference in their entireties). This gene replacement therapy targets GNE, which is defective in GNE myopathy (HIBM) patients, typically due to an autosomal recessive mutation of the GNE gene (see, e.g., Nemunaitis et al. *J Gene Med* 12, 403-12 (2010)). The GNE gene encodes the bi-functional enzyme UDP-GlcNAc 2-epimerase/ManNAc kinase. Thus, in some embodiments, therapy includes gene replacement therapy with wild type or modified GNE gene, genes involved in the sialic acid synthesis pathway, or other genes.

The appropriate dosage of any of these therapeutic agents, or any other agent of use to treat a hyposialylation disorder, can be determined using methods disclosed herein.

The disclosure is illustrated by the following non-limiting Examples.

EXAMPLES

Example 1

Materials and Methods

Materials:

Iodomethane, dimethyl sulfoxide anhydrous (DMSO), 2,5-dihydroxybenzoic acid (DHB), sodium hydroxide, trifluoroacetic acid (TFA), raffinose, sodium borohydrate, and sodium acetate were obtained from Sigma-Aldrich (St. Louis, Mo.). PNGase F, including denaturing buffer, digestion buffer and NP-40 were obtained from New England Biolabs (NEB, Ipswich, Mass.). EXTRACT-CLEAN™ SPE CARBOGRAPH® columns were obtained from Grace Davison Discovery Sciences (Deerfield, Ill.). SEP-PAK® Vac 3 cc C18 cartridges were from Waters (Milford, Mass.). p-lacto-N-hexaose (pLNH) was obtained from V-labs (Covington, La.). Methanol, chloroform and acetonitrile were from Fisher Scientific (Fair Lawn, N.J.).

Samples:

Normal serum or plasma samples were obtained from the collection at the Emory Clinical Biochemical Genetics Laboratory. A total of 150 serum or plasma specimens from normal population were used to collect the reference range for the N-glycans. Forty normal control serum or plasma was analyzed for the reference range of the O-glycans. The de-identified 6 sera from previously characterized patients with different CDG-II disorders were provided by Dr. Hudson Freeze (Sanford-Burnham Medical Research Institute, La Jolla, Calif.) and included COG4 (Ng et al. *Mol Genet Metab* 102, 364-367 (2011)), COG 7 (Wu et al. *Nat Med* 10, 518-523 (2004)), PGM1-CDG (mixed CDG-I and II with deficiency in nucleotide sugar metabolism) (Perez et al. *J Inher Metab Dis* 36, 535-542 (2013).) TMEM165-CDG (Foulquier et al. *Am J Hum Genet.* 91, 15-26 (2012)), and one CDG-IIx with mixed CDG-I and II (Mandato et al. *Pediatr Res* 59, 293-298 (2006)).

Sample Preparation for N-Glycan and O-Glycans:

Sample preparations for N- and O-glycans were carried out by PNGaseF digestion and β-elimination respectively as described before (Liu et al. *Mol Genet Metab* 106, 442-454 (2012)). 20 μL serum or plasma and 150 pmols of internal standard pLNH were used for N-glycan preparation and 10 μL serum or plasma and 1,250 pmols of internal standard raffinose was used for O-glycan preparation. All the purified glycans were lyophilized overnight to complete dryness.

Free Glycan Preparation:

Twenty μl of serum or plasma was diluted in 500 μl water and filtered through a size-exclusion Centricon with 10 kDa cutoff (Millipore, Billerica, Mass.). To separate the free glycans from large glycoproteins the sample was centrifuged at 10,000 rpm for 10 min at 4° C. The glycans from filtered mixture was then purified as described above.

Permethylation:

Both N- and O-glycans were permethylated as previously described with minor modifications (Faid et al. *Proteomics* 7, 1800-1813 (2007)). Briefly, a slurry of DMSO/NaOH was freshly prepared (0.4 ml) and was added to the dried glycan sample with 0.1 ml of iodomethane and mixed thoroughly for 60 min at room temperature. The permethylation reaction was then quenched by addition of 0.5 ml water and glycans were extracted by Chloroform (0.5 ml) and washed by water (0.5 ml) for 4 times and was then dried. The dried sample was further purified by the SEP-PAK® C18 column and then lyophilized overnight and ready for analysis by mass spectrometry.

N-Glycan and O-Glycan Profile Analysis by MALDI-TOF/TOF:

The permethylated N- or O-glycans were analyzed on an Applied Biosystem MALDI-TOF/TOF 4800 plus (Applied Biosystems, Foster City, Calif.) as described before (Liu et al. *Mol Genet Metab*, 106, 442-454 (2012)). 11 mg/ml 2,5-dihydroxybenzoic acid (DHBA) and 1 mM sodium acetate in 50% methanol was used as matrix buffer.

LC-MS/MS Conditions for Mucin Core 1 T-Antigen and Monosialyl ST-Antigen Quantification:

HPLC Separation of the small O-glycans released by β-elimination comprised of the core 1 disaccharide Galβ1-3GalNAc (T-antigen) and monosialyl-antigen (ST-antigen) was achieved with a Shimadzu Prominence 20AD LC and a Thermo gold 3-μm C18 column (2.0×100 mm) as described previously (Liu et al. *Mol Genet Metab* 106, 442-454 (2012)).

Preparation of Isotope Labeled Standards:

The purified milk sugar pLNH was labeled in the permethylation step as described above with either $^{12}C$ or $^{13}C$ by using either iodomethane-$^{12}C$ or iodomethane-$^{13}C$.

Example 2

Sample Stability

The stability of the glycans in serum and plasma was tested by storing three aliquots of serum or whole blood (plasma) from the same donor at RT for 0 hour (hr), 24 hr and 48 hr (Table A & B, below). Comparison at different time points demonstrated that the relative abundance of major N- and O-glycans in human serum or plasma was stable at RT for at least 48 hours, thus it is generally feasible to ship sera or whole blood at RT for glycan profiling tests. The percentage of CVs between relative abundance of N-glycans from these samples was less than 20%, and there was also no significance difference observed between the human serum and the human plasma (Tables A & B).

TABLE A

The Stability of N-Glycans of Total Plasma and Serum Glycoproteins at Room Temperature

| N-linked Glycans (m/z) | Plasma (% total glycan) | | | Serum (% total glycan) | | | Mean | SD | CV % |
|---|---|---|---|---|---|---|---|---|---|
| | 0 hr | 24 hr | 48 hr | 0 hr | 24 hr | 48 hr | | | |
| 1579.8 | 0.98 | 0.90 | 0.91 | 1.23 | 0.73 | 1.24 | 1.00 | 0.20 | 20 |
| 1661.8 | 0.14 | 0.13 | 0.12 | 0.16 | 0.12 | 0.17 | 0.14 | 0.02 | 14 |
| 1783.9 | 0.84 | 0.78 | 0.78 | 1.19 | 0.68 | 1.02 | 0.88 | 0.19 | 21 |
| 1835.9 | 0.10 | 0.06 | 0.10 | 0.09 | 0.06 | 0.09 | 0.08 | 0.02 | 21 |
| 1865.9 | 0.30 | 0.35 | 0.31 | 0.33 | 0.28 | 0.34 | 0.32 | 0.02 | 8 |
| 1982 | 0.40 | 0.45 | 0.42 | 0.51 | 0.33 | 0.42 | 0.42 | 0.06 | 14 |
| 1988 | 0.24 | 0.28 | 0.22 | 0.36 | 0.25 | 0.29 | 0.27 | 0.05 | 18 |
| 2156.1 | 0.09 | 0.12 | 0.12 | 0.10 | 0.10 | 0.15 | 0.11 | 0.02 | 18 |
| 2192.1 | 0.37 | 0.35 | 0.33 | 0.51 | 0.34 | 0.32 | 0.37 | 0.07 | 20 |
| 2227.1 | 0.89 | 0.94 | 0.92 | 0.75 | 0.78 | 0.81 | 0.85 | 0.08 | 9 |
| 2285.2 | 0.12 | 0.12 | 0.15 | 0.05 | 0.11 | 0.07 | 0.10 | 0.03 | 34 |
| 2396.2 | 0.26 | 0.47 | 0.65 | 0.74 | 0.50 | 0.52 | 0.52 | 0.16 | 31 |
| 2431.2 | 3.81 | 3.90 | 4.26 | 3.64 | 3.37 | 3.29 | 3.71 | 0.36 | 10 |
| 2605.3 | 0.79 | 0.72 | 0.90 | 0.81 | 0.85 | 0.69 | 0.79 | 0.08 | 10 |
| 2792.4 | 13.18 | 14.61 | 15.16 | 14.38 | 14.96 | 12.46 | 14.12 | 1.07 | 8 |
| 2966.5 | 1.34 | 1.60 | 1.65 | 1.56 | 1.67 | 1.33 | 1.52 | 0.15 | 10 |
| 3241.6 | 0.35 | 0.48 | 0.51 | 0.34 | 0.47 | 0.40 | 0.42 | 0.07 | 17 |
| 3415.7 | 0.18 | 0.13 | 0.15 | 0.21 | 0.25 | 0.11 | 0.17 | 0.05 | 31 |
| 3602.8 | 1.41 | 1.59 | 2.09 | 1.44 | 1.82 | 1.16 | 1.59 | 0.33 | 21 |
| 3776.9 | 1.01 | 1.00 | 1.52 | 0.88 | 1.25 | 0.80 | 1.07 | 0.27 | 25 |

TABLE B

The Stability of O-Glycan of Total Plasma and Serum Glycoprotein at Room temperature

| O-linked Glycans | Plasma (uM) | | | Serum (uM) | | | Mean | SD | CV % |
|---|---|---|---|---|---|---|---|---|---|
| | 0 hr | 24 Hr | 48 hr | 0 hr | 24 hr | 48 hr | | | |
| T-antigen | 0.80 | 0.89 | 0.89 | 0.91 | 0.86 | 0.83 | 0.86 | 0.04 | 0.13 |
| Monosialy T antigen | 18.45 | 18.05 | 18.65 | 17.7 | 18.4 | 17.4 | 18.11 | 0.48 | 10.4 |

Example 3

Precision and Recovery

The consistency of permethylation and the recovery of glycans during the glycans purification steps were evaluated using isotope labeled standards. First, the light ($^{12}C$) and heavy ($^{13}C$) isotope-labeled internal standards were permethylated as described above. Equal aliquots of light- and heavy-labeled pLNH were prepared separately and mixed together and analyzed by MALDI-TOF. The ratio of peak areas of light- and heavy-labeled standards was 1.02 and the partial permethylated pLNH was <5%, indicating that the permethylation reactions were >95% complete and there was minimal variation in permethylation. Thus, the measured intensity of permethylated standard accurately reflects the molar ratio of starting material. Next, the unlabeled pLNH 500 pmol was spiked into the plasma and carried through the whole process. After these final steps, 500 pmols $^{13}C$-labeled standard were added to the mixture before it was analyzed by MALDI-TOF. The ratio of unlabeled standard (m/z 1375) and peak area of $^{13}C$-labeled standard (m/z 1395) was 0.97, and the recovery of pLNH through purification was estimated at 97%. The high recovery rate indicates that the purification steps are very efficient and monitoring the signal of known amount of internal standard should be sufficient to monitor the efficiency of these steps. The fragmentation pattern of the glycans were obtained using MALDI-TOF/TOF mode for additional information on sugar component and structure.

The variations of interday and intraday runs of O-glycan and N-glycan analysis were measured to evaluate the test precision and reproducibility. Intraday CVs of the four most abundant N-glycans, T-antigen and ST-antigens were less than 20%. Interday CVs were also less than 20% (Table 1).

TABLE 1

Precision of N- and O-Glycan Analysis by MALDI-TOF in Control Plasma

| Structure | N-glycan | m/z | Interassay(n = 20) | | | Intra-assay(n = 10) | | |
|---|---|---|---|---|---|---|---|---|
| | | | Median (%) | SD | % CV | Median (%) | SD | % CV |
| | Neu5Ac2Hex5HexNAc4 (disialo biantennary) | 2792.4 | 15.7 | 1.8 | 11 | 15.7 | 1.0 | 6 |
| | Neu5Ac2Fuc1Hex5HexNAc4 (disialo biantennary fucosylated) | 2966.5 | 1.6 | 0.2 | 11 | 1.2 | 0.1 | 9 |
| | Neu5Ac2Hex6HexNAc5 (disialo triantennary) | 3241.6 | 0.7 | 0.1 | 20 | 0.7 | 0.1 | 17 |
| | Neu5Ac3Hex6HexNAc5 (trisialo triantennary) | 3602.8 | 2.4 | 0.3 | 12 | 2.6 | 0.4 | 18 |

| N/A | O-glycan | MRM | Interassay(n = 20) | | | Intra-assay(n = 10) | | |
|---|---|---|---|---|---|---|---|---|
| | | | Median (µM) | SD | % CV | Median (µM) | SD | % CV |
| | T-antigen | 534/298 | 0.74 | 0.08 | 11 | 0.73 | 0.06 | 7.8 |
| | Monosialylated-T-antigen | 895/520 | 19.9 | 3.4 | 17 | 23.2 | 1.4 | 6.0 |

■: GlcNAc, ●: Man, ◎: Gal, ◆: NeuNAc, ▲: Fuc

Example 4

O-Glycan Profiles of Total Serum or Plasma Total Glycoproteins

O-glycan profiles of 40 normal plasma or serum samples were analyzed, along with 6 CDG-II samples. A small amount of T-antigen was spiked into a normal plasma sample and was run as a positive control with each O-glycan analysis to help identify all the major O-glycan species shown in FIG. 1A, including T-antigen (m/z 534), monosialyl ST-antigen (ST) (m/z 895), disialyl-T-antigen (m/z 1256), monosialyl core 2 (m/z 1344) and disialyl core 2 (m/z 1705), with ST-antigen at m/z 895 as the most abundant species. The relative quantity of monosialyl ST-antigen and disialyl-T-antigen were estimated by comparing their intensity to the internal standard (raffinose at m/z 681). A clear reduction of abundance could be detected by semi-quantifying ST-antigen and disialyl-T-antigen in 3 COG patients (red circles) comparing to controls (blue triangles) with MALDI-TOF analysis (FIG.

1B)(Faid et al. *Proteomics* 7, 1800-1813 (2007)). However, the abundance of T-antigen at m/z 534 is difficult to evaluate by MALDI-TOF.

Figure 2A:
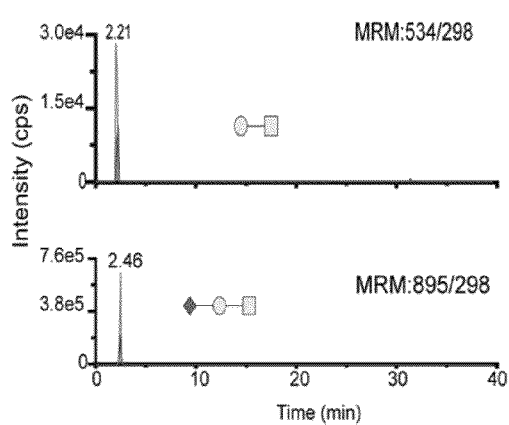
FIGS. 2A-2D: Plasma O-glycan LC-MSMS quantification and comparison study between 40 healthy control subject and 6 CDG-II patients' sera.
Figure 2B:
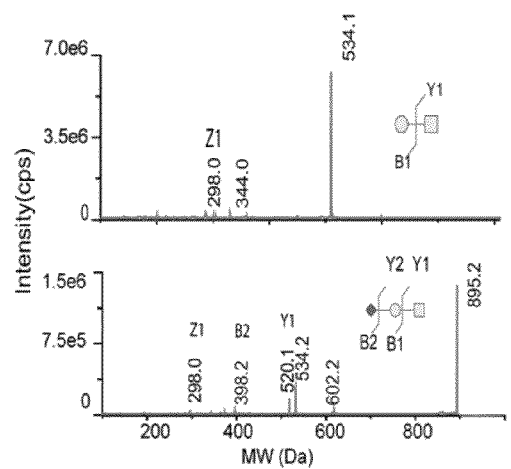
Figure 2C:
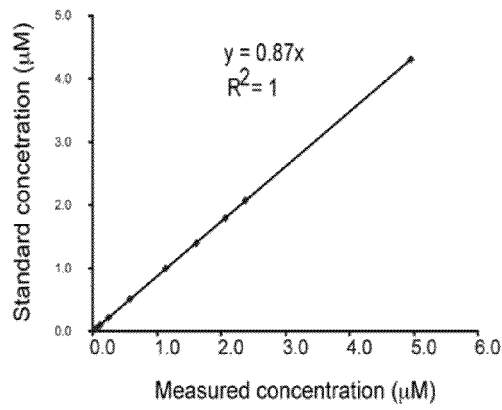
Figure 2D:
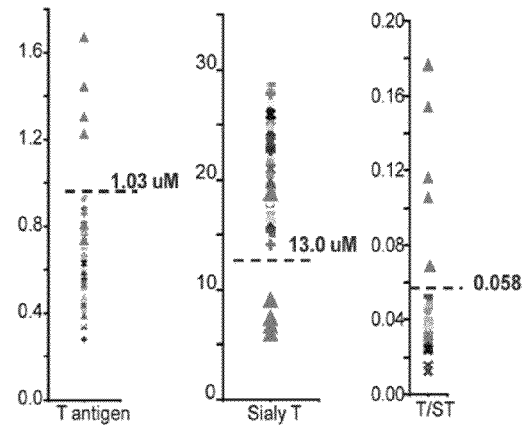

In order to achieve better quantification of serum or plasma O-glycans, a LC-MS/MS method was developed to quantify T-antigen and monosialylated ST-antigen. The chromatograms of extracted multiple reaction monitoring (MRM) for T-antigen, and monosialylated ST-antigen are shown in FIG. 2A. The specificities of the MRM transitions for each glycan are supported by MRM-triggered enhanced parent ion (EPI) profiles for each O-glycan shown in FIG. 2B. Pure T-antigen standard was run to evaluate the recovery, limit of quantification and linearity of the LC-MSMS analysis (FIG. 2C). The analytical measurement range of T-antigen was 0.0625-5 μM and recovery was >90%. The ratio between T- and monosialylated ST-antigens was also obtained to evaluate the sialylation of core 1 O-glycans. The reference ranges of both T- and monosialylated ST-antigens, along with the T- and monosialylated ST-antigen ratio, were obtained from 40 normal control sera or plasma. All six positive CDG samples have relatively high T-antigen and low monosialylated ST-antigen (FIG. 2D). The distinction between affected patients and control was best achieved by measuring T/monosialylated ST-antigen ratio. The T/ST ratio of three known COG patients were at 0.17 (COG4), 0.11 (COG7, patient 1), 0.11 (COG7, patient 2) with the reference interval of the T/ST-antigen ratio from controls at 0-0.056. All three known COG samples had low monosialylated ST-antigen levels, and increased T/ST-antigen ratio. However, an increased T-antigen level was detected in the COG4-CDG patient, but not in two COG7-CDG samples (Table 2).

TABLE 2

Quantification of Serum O-glycans in Patients with CDG-II and Normal Controls

| O-glycan | T(μM) | Monosialyl-T(μM) | T/Monosialyl-T ratio |
|---|---|---|---|
| Control | <=1.03 | >=13 | <=0.058 |
| TMEM165 | 1.67 | 9.45 | 0.177 |
| PGM1 | 1.44 | 9.38 | 0.154 |
| (mixed type I and II) | | | |
| COG4 | 1.23 | 6.95 | 0.176 |
| COG7 p1 | 0.80 | 7.67 | 0.105 |
| COG7 p2 | 0.73 | 6.33 | 0.116 |
| Mixed type I and II | 1.30 | 19.02 | 0.068 |

Without being bound by theory, relatively low T-antigen in these two samples from patients with COG7 deficiency could reflect more severely affected Golgi protein transporting and more severe clinical phenotype in these patients (Wu et al. *Nat Med* 10, 518-523 (2004)). Increased T/ST-antigen ratios were detected in PGM1-CDG, which is similar to what was reported in galactosemia (Liu et al. *Mol Genet Metab* 106, 442-454 (2012)). O-glycan quantification in TMEM165-CDG showed significant increase of T-antigen, mildly reduced monosialylated ST-antigen, and increased T/ST-antigen ratio, providing evidence that TMEM165-CDG is a multiple glycosylation disorder (Table 2). Increased T/ST-antigen ratio was found, reflecting mild undersialylation of O-linked protein glycosylation in the serum from a known patient with CDG-IIx. Without being bound by theory, the finding of undersialylation of O-glycans and possible deficiencies of multiple Golgi glycosyltransferases provides evidence that this new mixed type I and type II is likely related to a deficiency in general Golgi functions and affect multiple Golgi protein glycosylation functions.

The abundance of T antigen and monosialylated ST-antigen in the plasma or serum are of several orders of difference, and MALDI-TOF analysis is very limited in quantifying T and ST. The level of sialylation of O-glycans are reduced in almost all the known multiple glycosylation disorders (Wu et al. *Nat Med* 10, 518-523 (2004); Mohamed et al. *J Inherit Metab Dis* 34, 907-916 (2011)). Therefore accurate quantification of T-antigen, the only nonsialylated O-glycan detectable in plasma or serum glycoproteins, is critical. Disclosed herein is an LC-MS/MS method to quantify serum or plasma T- and ST-antigens. The disclosed methods provide detection of mild undersialylation of O-glycans in total plasma or serum glycoproteins, otherwise undetectable by MALDI-TOF analysis, by utilizing the T/ST-antigen ratio. Using this LC-MS/MS method, undersialylation of O-glycosylation was demonstrated in this disorder. In the case of COG7 deficiency, both T-antigen and monosialylated ST-antigen were reduced. The results show that the reason that T-antigen appears increased in COG7-CDG by MALDI-TOF is due to relative low intensity of monosialylated ST-antigen rather than increased T-antigen.

It is estimated that 2-3% of the genome encodes for genes important in glycosylation processes. A reliable clinical biochemical screening test to accurately detect and profiling CDG-IIx improves the diagnostic yield of CDG-IIx. The disclosed methods provide a clear distinction between CDG positive samples and the control population.

Example 5

T/ST Ratio in GNE Myopathy and Glomerulopathies

The following example shows that the ratio of plasma and/or serum mucin core 1 T-antigen to monosialylated ST antigen (T/ST ratio) is an effective biomarker for diagnosis and prediction of treatment outcome for GNE myopathy, and likely for other hyposialylation disorders, such as kidney hyposialylation disorders. For these studies, a cut-off value of 0.06 was used to diagnose hyposialylation.

The quantification of the T/ST ratio was carried out using the O-glycan quantification methods disclosed in Liu et al. *Mol Genet Metab* 106, 442-454 (2012). Briefly, O-linked glycans from human serum or plasma total glycoproteins were released by sodium hydroxide with sodium borohydrate and desalted by ion-exchange column and then permethylated before the quantity of T-antigen and monosialyl ST-antigen was measured using LC-MS/MS method. Plasma samples from 40 normal controls were used to establish the normal range for the T/ST ratio at <0.056. A cut-off of 0.06 was used to diagnose hyposialylation of O-linked protein glycosylation in human plasma or serum.

Of the 38 tested plasma samples from patients with GNE myopathy, 35 samples were in the abnormal T/ST ratio range (0.06 or higher), indicating hyposialylation. Representative results are shown in the tables below:

| Patient | Plasma T/ST | T (uM) | ST (uM) | Serum T/ST | Serum T (uM) | Serum ST (uM) |
|---|---|---|---|---|---|---|
| Normal Range | <0.06 | 0.22-1.14 | 11.7-31.4 | | | |
| GNE Myopathy Patients: | | | | | | |
| NH00002 | 0.10 (bl) | 1.34 | 12.6 | 0.11 | 2.25 | 17.2 |
| | 0.09 (3 mo) | 1.27 | 14.6 | | | |
| | 0.14 (6 mo) | 1.77 | 12.9 | | | |
| NH00005 | 0.08 (bl) | 1.02 | 14.0 | | | |
| | 0.08 (6 mo) | 1.22 | 16.00 | | | |
| NH00010 | 0.10 (bl) | 1.24 | 11.8 | 0.11 | 2.46 | 19 |
| | 0.09 (3 mo) | 0.79 | 18.5 | | | |
| | 0.10 (9 mo) | 1.44 | 14.1 | | | |
| NH00013 | 0.13 (bl) | 1.09 | 8.1 | | | |
| | 0.07 (6 mo) | 1.14 | 17.30 | | | |
| | 0.07 (9 mo) | 0.85 | 12.00 | | | |
| NH00014 | 0.07 (bl) | 0.85 | 12.2 | | | |
| | 0.08 (6 mo) | 1.34 | 15.0 | | | |
| NH00016 | 0.05 (bl) | 0.70 | 13.0 | 0.06 | 0.97 | 14.8 |
| | 0.10 (3 mo) | 1.66 | 16.7 | 0.08 | 1.25 | 13.2 |
| | 0.07 (6 mo) | 0.92 | 12.4 | | | |
| NH00020 | 0.08 (bl) | 1.18 | 15.3 | | | |
| | 0.10 (6 mo) | 1.78 | 15.7 | | | |
| NH00021 | 0.09 (bl) | 0.89 | 10.4 | | | |
| | 0.08 (6 mo) | 1.20 | 15.80 | | | |
| NH00028 | 0.09 (bl) | 1.56 | 17.1 | | | |
| | 0.11 (6 mo) | 1.57 | 14.00 | | | |
| NH00032 | 0.07 | 0.98 | 14.9 | 0.09 | 2.39 | 22.7 |
| NH00033 | 0.09 | 1.47 | 15.8 | | | |
| NH00036 | 0.09 | 1.29 | 14.2 | | | |
| NH00037 | 0.06 | 1.11 | 17.4 | | | |
| NH00038 | 0.06 | 1.76 | 11.8 | | | |
| NH00042 | 0.09 | 0.79 | 8.5 | | | |
| NH00043 | 0.06 (bl) | 0.83 | 12.9 | | | |
| | 0.06 (3 mo) | 1.18 | 17.1 | | | |
| sia13 | 0.07 | 0.69 | 9.7 | | | |
| sia14a | 0.1 | 0.22 | 2.2 | | | |
| sia14b | 0.05 | 0.40 | 8.9 | | | |
| sia16 | 0.08 | 1.00 | 12.0 | | | |
| SIA79 | 0.06 | 1.05 | 16.5 | | | |
| SIA80 | 0.10 | 1.37 | 13.3 | | | |
| SIA81 | 0.11 | 1.53 | 13.7 | | | |

| | Normal range |
|---|---|
| | Abnormal range-hyposialylated |
| bl | Baseline (first NIH visit) |
| 3 mo | 3 months NIH visit after baseline |
| 6 mo | 6 months NIH visit after baseline |
| 9 mo | 9 months NIH visit after baseline |

As shown in the above Table, even though individual T antigen or monosialylated ST antigen values can be in the normal range for a GNE myopathy patient, the T/ST ratio is in almost all cases abnormal for subject with GNE myopathy. Follow-ups with the three patients whose samples were in the normal range revealed that: (a) one patient (SIA79) was self-administering off-label ManNAc, (b) one patient (Sia 14a before therapy and Sia14b the same patient after therapy) had received IVIG therapy to increase sialylation (before this therapy the T/ST ratio was 0.1, and after the therapy it became 0.05), and (c) one patient (NH00016) had received sialic acid one month before the test (her T/ST ratio was 0.05 after treatment, but after three months without medication, her ratio increased to abnormal range of 0.7). These follow-ups further show the sensitivity and reliability of this ratio in diagnosing and monitoring hyposialylation, and determining the effectiveness of therapeutic agents.

The table indicated plasma T/ST ratios in all patients and serum T/ST ratios in some patients. The serum T/ST ratio is also abnormal, indicating that patient's serum can also be used for the T/ST biomarker.

Plasma or serum T/ST ratios from eighteen patients with unexplained glomerulopathies were also tested. Twelve patients had ratios in the normal range (≤0.06), and six patients had ratios that indicated hyposialylation (>0.06). Kidney biopsies were available from four patients from this group. Lectin histochemistry on paraffin embedded slides of these kidney biopsies those (because lectins are sugar-binding protein they can help to determine glomerular sialylation status, as described in Kakani et al. Am J Pathol 180: 1431-40, 2012) showed normal glomerular sialylation in two patients (Renal 2 and Renal 5) with T/ST ratios in the normal range; while glomerular hyposialylation was detected in biopsy samples of two other patients (Renal 1 and Renal 3) which had increased T/ST ratios (of 0.09 and 0.07, respectively). The results are shown in the table below.

Kidney biopsies of 40 patients with different glomerular diseases were also analyzed by lectin staining (but no plasma or serum was available). Eight of these were hyposialylated, indicating that glomerular hyposialylation exists in this patient population. These results suggest that the plasma or serum T/ST ratio can be a reliable biomarker for detecting glomerular hyposialylation.

| Patient | Plasma (p) or Serum (s) T/ST ratio | T (uM) | ST (uM) | Lectin staining of kidney biopsy |
|---|---|---|---|---|
| Normal range | <0.06 | 0.22-1.14 | 11.7-31.4 | |
| Renal 1 | 0.09 (p) | 1.22 | 13.4 | hyposialylated glomeruli |
| Renal 2 | 0.04 (p) | 0.97 | 19.6 | normal sialylation |
| Renal 3 | 0.07 (p) | 1.18 | 13.8 | hyposialylated glomeruli |
| Renal 4 | 0.11 (s) | 2.59 | 20.5 | ND |
| Renal 5 | 0.05 (s) | 1.49 | 25.3 | normal sialylation |
| Renal 6 | 0.06 (s) | 1.7 | 24.7 | ND |
| Renal 7 | 0.07 (s) | 1.86 | 21.2 | ND |
| Renal 8 | 0.07 (s) | 2.03 | 25.3 | ND |
| Renal 9 | 0.03 (s) | 0.59 | 19.7 | ND |
| Renal 10 | 0.04 (s) | 1.32 | 29 | ND |
| Renal 11 | 0.03 (s) | 0.67 | 17 | ND |
| Renal 12 | 0.09 (s) | 1.33 | 12.4 | ND |
| Renal 13 | 0.04 (s) | 0.83 | 18.1 | ND |
| Renal 14 | 0.03 (s) | 1.02 | 26 | ND |
| Renal 15 | 0.04 (s) | 0.77 | 17.8 | ND |
| Renal 16 | 0.03 (s) | 0.91 | 24.1 | ND |
| Renal 17 | 0.03 (s) | 0.92 | 24.4 | ND |
| Renal 18 | 0.03 (s) | 0.53 | 15.5 | ND |

| | Abnormal range-hyposialylated |
|---|---|
| ND | Not determined/no biopsy available |

Example 6

Additional Methods

Chemicals:

Jodomethane, dimethyl sulfoxide anhydrous (DMSO), 2,5-dihydroxybenzoic acid (DHB), sodium hydroxide, trifluoroacetic acid (TFA), raffinose, sodium borohydrate, and sodium acetate were all purchased form Sigma-Aldrich (St. Louis, Mo., USA). N-Glycosidase F (PNGase F), including denaturation buffer, digestion buffer, and NP-40 buffer were all purchased from New England Biolabs (Ipswich, Mass.). EXTRACT-CLEAN™ SPE CARBOGRAPH® columns were purchased from Grace Davison Discovery Science (Deerfield, Ill.). The SEP-PAK® Vac C18 cartridge 3 cc was from Waters (Milford, Mass.). The P-Lacto-N-hexaose (pLNH) was from V-labs (Covington, La.). Acetonitrile, chloroform, methanol, sodium hydroxide (w/w, 50%), and sodium acetate were all from Fisher Scientific (Fairlawn, N.J., USA).

Preparation of O-Glycans for Analysis:

O-glycans were released from plasma glycoproteins and prepared for analysis essentially as described by Carlson (J Biol Chem 243: 616-626, 1968; Liu et al. *Mol Genet Metab* 106, 442-454 (2012)), with modifications as described. An internal standard (1250 pmol raffinose in 5 µL) was added to 10 µL of plasma and 65 µl water for a final volume of 100 µL. Next, 100 µL of freshly prepared 2M sodium borate in 0.1M sodium hydroxide was added to denature the serum proteins and release the O-glycans; the mixture was incubated at 45° C. for 16 hours to ensure complete reaction. The reaction was neutralized by drop wise addition of 1.6 mL of a 0.25M acetic acid-methanol solution, and the O-glycans were extracted in methanol. Finally, the extracted glycans were desalted through ion-exchange AG 50W-X8 resin (Bio-Rad, Hercules, Calif.) following the manufacture's instruction and lyophilized overnight. The dried samples were dissolved in DMSO for permethylation.

Permethylation:

Both N-glycans and O-glycans were permethylated as previously described with minor modification (Guillard et al. *Clin Chem* 57, 593-602 (2011)). Briefly, four NaOH pellets (approximately 375 mg) were crushed in 10 ml anhydrous DMSO, 0.5 µL water, 0.4 ml of this slurry and 0.1 ml CH3I were added to the dried glycans and the mixture was shaken vigorously for one hour. The mixture was extracted five times sequentially with a mixture of 200 µL water and 600 µL chloroform. Finally, the combined chloroform phases were dried under nitrogen in the chemical hood (30 mins) and the permethylated N- and O-glycans were resuspended in 50 µL of 50% methanol and further purified through a C18 Stage Tip (Thermo Scientific, West Palm Beach, Fla.) as described.

Quantification of O-Linked Glycans Core 1 T-Antigen and Sialyl-ST Antigen by Tandem Mass Spectrometry Coupled with High-Performance Liquid Chromatography (HPLC-MS/MS):

HPLC separation of O-linked glycans was achieved with a Shimadzu Prominence 20AD LC and a Thermo gold 3-µm C18 column (2×100 mm). The binary method used buffer A (acetonitrile:formic acid:water; 1:0.1:99 (v:v:v)) and buffer B (acetonitrile:formic acid:water; 99:0.1:1 (v:v:v)) with a flow rate at 0.25 ml/min under the following gradient conditions: 0-20 min, 50% to 80% buffer B; 20-28 min, 98% buffer B; 28-39 min, 50% buffer B. An injection volume of 10 µl was used for analysis of each sample.

The API-QTRAP® 5500 tandem mass spectrometry conditions were as follows: ion source: EPI positive mode; curtain gas: 25; ion source: 5500; source temperature: 600. MRM transitions for core1 T-antigen and monosialyl-T-antigen were: m/z 534/298 and m/z 895/520. The parent ion of the T antigen is 534, the parent ion of the monosialylated ST antigen is 895, and the fragment ions are 298 and 520, respectively.

Calibration curves were constructed with 6 concentrations of Tn-antigen (from 0.0625 to 5 µM). The ST value is based on the ratio of the ST over the T peak area, times the T absolute value.

Example 7

Sialylation of Thomsen-Friedenreich Antigen is a Noninvasive Blood-Based Biomarker for GNE Myopathy GNE myopathy is an adult-onset progressive myopathy, resulting from mutations in GNE, the key enzyme of sialic acid synthesis. The exact pathomechanism of GNE myopathy is not known, but likely involves aberrant sialylation. GNE myopathy muscle biopsies demonstrated hyposialylation of O-linked glycans. Therefore, the O-linked glycome of patients' plasma proteins was analyzed using mass spectrometry. Most patients showed an increased core 1 O-linked glycan, Thomsen-Friedenreich (T)-antigen, and/or decreased amounts of its sialylated form, ST-antigen. Moreover, all patients had increased ratios of T-antigen to ST-antigen compared to unaffected individuals. Importantly, the T/ST ratios were normalized in a patient treated with intravenous immunoglobulins as a source of sialic acid, indicating response to therapy. These findings highlight plasma T/ST ratios as a robust blood-based biomarker for GNE myopathy, and can help explain the pathology and course of the disease.

Materials & Methods

Patients:

GNE myopathy patients were enrolled in either clinical protocol NCT01417533, 'A Natural History Study of Patients with Hereditary Inclusion Body Myopathy', or protocol NCT00369421, 'Diagnosis and Treatment of Inborn Errors of Metabolism and Other Genetic Disorders.' Peripheral blood samples were obtained and used for serum or plasma preparations. Genomic DNA was isolated from white blood cell pellets, and used for GNE mutation analysis for molecular validation of the GNE myopathy diagnosis, as shown in the table below. Peripheral blood from healthy donors without clinical complaints at the time of donation were also obtained.

TABLE 5

Figure 6A:
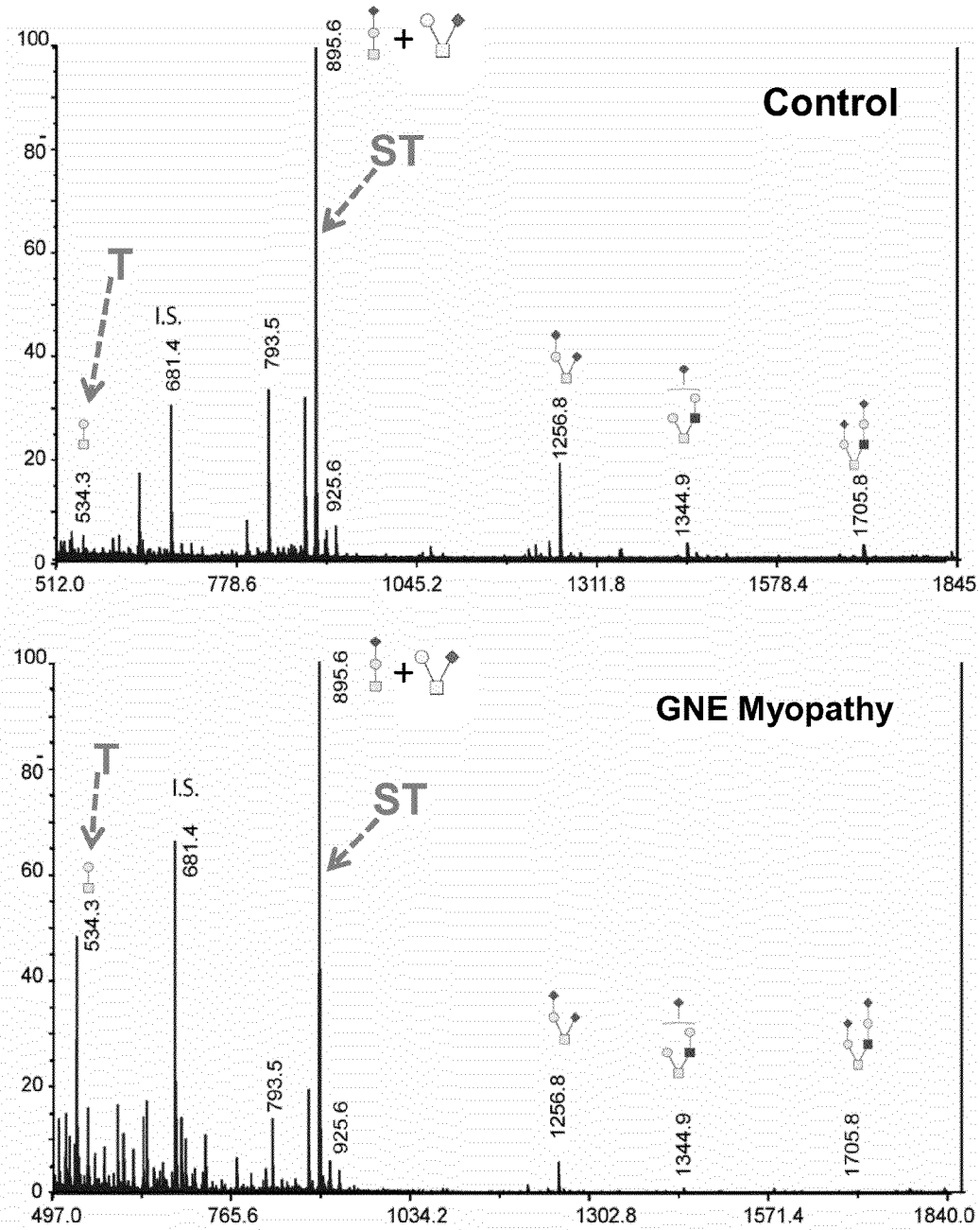
FIGS. 6A-6B. Plasma O-glycan MALDI-TOF/TOF profiles and quantitative comparison of T and monosialylated ST antigens of control and GNE myopathy patients.
Figure 6B:
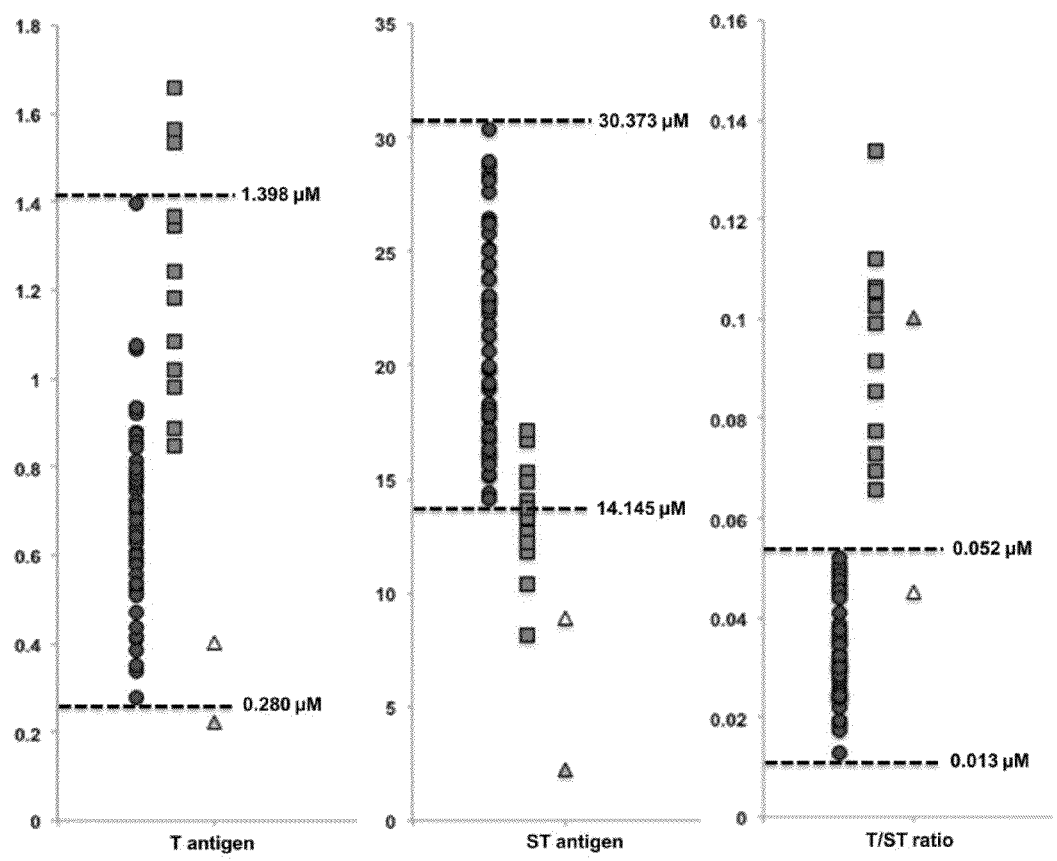

Absolute T- and ST-values as visualized in FIG. 6B

|  | T/ST | T-(uM) | ST-(um) |
|---|---|---|---|
|  | Normal Range | | |
|  | 0.013-0.052 | 0.280-1.398 | 14.145-30.373 |
| control1 | 0.03600597 | 0.88012959 | 24.44399043 |
| control2 | 0.024737589 | 0.588552916 | 23.79184665 |
| control3 | 0.050357143 | 0.761339093 | 15.1187905 |
| control4 | 0.032507317 | 0.642548596 | 19.76627584 |
| control5 | 0.025486765 | 0.411987041 | 16.16474456 |
| control6 | 0.031530351 | 0.750539957 | 23.8037295 |
| control7 | 0.029221739 | 1.772138229 | 26.42341804 |
| control8 | 0.046083558 | 0.664146868 | 14.4117967 |
| control9 | 0.049351003 | 1.398488121 | 28.33758262 |
| control10 | 0.038265244 | 0.88012959 | 23.00075734 |
| control11 | 0.030472441 | 0.696544276 | 22.85817135 |
| control12 | 0.027367188 | 0.610151188 | 22.29499059 |
| control13 | 0.046306667 | 0.745140389 | 16.09142792 |
| control14 | 0.018971846 | 0.524298056 | 27.63558443 |
| control15 | 0.037186567 | 1.069114471 | 28.75001788 |
| control16 | 0.038818182 | 0.6587473 | 16.97007097 |
| control17 | 0.024343887 | 0.530777538 | 21.80331903 |
| control18 | 0.035924419 | 0.599352052 | 16.68369524 |
| control19 | 0.049971264 | 0.761339093 | 15.23553791 |
| control20 | 0.025650000 | 0.510259179 | 19.89314539 |
| control21 | 0.021967647 | 0.415766739 | 18.92632095 |
| control22 | 0.030728933 | 0.772138229 | 25.12740157 |
| control23 | 0.024683866 | 0.471382289 | 19.09677734 |
| control24 | 0.030382483 | 0.782937365 | 25.76936702 |
| control25 | 0.025054667 | 0.534017279 | 21.31408435 |
| control26 | 0.044735941 | 0.923326134 | 20.63947034 |
| control27 | 0.025197952 | 0.57775378 | 22.92860049 |
| control28 | 0.030213308 | 0.874730022 | 28.9518123 |
| control29 | 0.035377778 | 1.074514039 | 30.37257019 |
| control30 | 0.024160494 | 0.556155508 | 23.01921109 |
| control31 | 0.017500000 | 0.279697624 | 15.98272138 |
| control32 | 0.024002206 | 0.435205184 | 18.13188278 |
| control33 | 0.019414154 | 0.387149028 | 19.94158649 |
| control34 | 0.012814286 | 0.336933045 | 26.29354869 |
| control35 | 0.024096774 | 0.63174946 | 26.21717973 |
| control36 | 0.019197519 | 0.350431965 | 18.25402355 |
| control37 | 0.030564741 | 0.858531317 | 28.08894459 |
| control38 | 0.048591633 | 0.93412527 | 19.223994 |
| control39 | 0.052225564 | 0.815334773 | 15.61179453 |
| control40 | 0.032775000 | 0.534017279 | 16.29343337 |
| control41 | 0.040855824 | 0.701943844 | 17.1809984 |
| control42 | 0.035728827 | 0.63174946 | 17.68178546 |
| control43 | 0.034503188 | 0.842332613 | 24.41318208 |
| control44 | 0.032090347 | 0.723542117 | 22.54703345 |
| control45 | 0.028532927 | 0.712742981 | 24.97966594 |
| control46 | 0.037646341 | 0.680345572 | 18.07202363 |
| Control47 | 0.029976062 | 0.534017279 | 17.81479103 |
| Control48 | 0.047432705 | 0.799136069 | 16.84778604 |
| Control49 | 0.045426647 | 0.642548596 | 14.14475077 |
| Control50 | 0.043903104 | 0.93412527 | 21.27697553 |
| mean | 0.032966801 | 0.684082073 | 21.1724522 |
| SD | 0.009865643 | 0.211104208 | 4.441626615 |

TABLE 5-continued

Absolute T- and ST-values as visualized in FIG. 6B

| Patient | GNE allele 1 | GNE allele 2 | T/ST | T (uM) | ST (uM) |
|---|---|---|---|---|---|
| | | | Normal Range | | |
| | | | <0.052 | 0.280-1.398 | 14.145-30.373 |
| GNE-2 | c.1909 + 5G > A | p.V696M | 0.10652626 | 1.34449244 | 12.62123039 |
| GNE-5 | p.M712T | p.M712T | 0.07277276 | 1.02051836 | 14.02335691 |
| GNE-10 | p.D213V | p.V696M | 0.10549956 | 1.24190065 | 11.77161965 |
| GNE-13 | p.M712T | p.M712T | 0.13382721 | 1.08531317 | 8.10980918 |
| GNE-14 | p.V216A | p.A631V | 0.06943573 | 0.84773218 | 12.20887551 |
| GNE-16 | p.M712T | p.M712T | 0.09924569 | 1.65766739 | 16.70266379 |
| GNE-20 | p.W513X | p.A631V | 0.07734388 | 1.18250540 | 15.28893296 |
| GNE-21 | p.D378Y | p.A631V | 0.08537143 | 0.88552916 | 10.37266416 |
| GNE-28 | p.R129X | p.V696M | 0.09140743 | 1.56317495 | 17.10118034 |
| GNE-32 | p.M712T | p.M712T | 0.06578169 | 0.98002160 | 14.89809162 |
| GNE-980 | p.M712T | p.M712T | 0.10246480 | 1.36609071 | 13.33229279 |
| GNE-981 | p.M712T | p.M712T | 0.11202826 | 1.53347732 | 13.68830792 |
| GNE-914a | p.M712T | p.M712T | 0.10040766 | 0.22084233 | 2.19945707 |
| GNE-914b* | p.M712T | p.M712T | 0.04536585 | 0.40172786 | 8.85529158 |

(normal ranges are highlighted in grey)

Whole Blood Sample Preparations:

Serum (non-gel serum separator tube, clot activator) and plasma ($K_2$EDTA-anticoagulant) were isolated from whole blood using standard protocols, followed by albumin and IgG depletion using a Qproteome Albumin/IgG depletion kit (Qiagen). Protein purification and concentration was performed with micron Ultra-0.5 mL Centrifugal Filters (EMD Millipore, Billerica, Mass.). Selected control samples were desialylated by incubation with 1 µl (50 U) neuraminidase for 1 hour at a 37° C. (P0720, New England Biolabs, Ipswich, Mass.). This neuraminidase (cloned from *Clostridium perfringens* and overexpressed in *E. coli*) catalyzes the hydrolysis of α2-3, α2-6, and α2-8 linked N-acetyl-neuraminic acid residues from glycoconjugates.

Immunoblotting:

Serum (10-40 µg) proteins were boiled at 95° C. for 5 min in Laemmli Sample buffer (Bio-Rad Laboratories) and electrophoresed on 4-12% Tris-Glycine gels (Invitrogen), followed by electroblotting onto nitrocellulose membranes (Invitrogen). The membranes were incubates with Ponceau S red according to the manufacturer's protocol (Sigma-Aldrich, St Louis, Mo.) to visualize equal loading and transfer of proteins in each lane. The membranes were either probed with primary antibodies against NCAM or with different lectins. Two antibodies against NCAM were evaluated H-300 (sc-10735) and RNL-1 (sc-53007) (Santa Cruz Biotechnology, Santa Cruz, Calif.), whose binding was visualized by IRDYE® 800CW conjugated secondary anti-mouse (for RNL-1) or anti-rabbit (for H-300) antibodies (LI-COR® Biosciences, Lincoln, Nebr., USA). The antigen-antibody complexes were visualized with the LI-COR® ODYSSEY® Infrared imaging system (LI-COR® Biosciences). For lectin probing (FIG. 9A-9D), biotinylated SNA (*Sambucus nigra* agglutinin) and WGA (wheat germ agglutinin) were purchased from Vector Laboratories (Burlingame, Calif.), and biotinylated VVA (*Vicia villosa* agglutinin) was purchased from EY Laboratories (San Mateo, Calif.). IRDYE® 680Streptavidin (LI-COR® Biosciences, Lincoln, Nebr.) was used to bind to biotin-labeled proteins and visualized with a LI-COR® Odyssey Infrared imaging system (LI-COR® Biosciences).

Muscle Lectin Histochemistry:

Paraffin embedded sections (5 µm) were obtained from control biceps muscle (National Disease Research Interchange (NDRI), Philadelphia, Pa.), right gastrocnemius muscle from patient GNE-21 (carrying GNE mutations D378Y and A631V), and left biceps muscle from patient GNE-28 (carrying ONE mutations R129X and V696M). The sections were deparaffinized in HEMO-DE® (Scientific Safety Solvents, Keller, Tex.), rehydrated in a series of ethanol solutions, followed by antigen retrieval (by microwaving in 0.01M Sodium Citrate, pH 6.4) and blocking in CARBO-FREE® Blocking solution (Vector Laboratories, Burlingame, Calif.). The slides were incubated at 4° C. overnight with each fluorescein isothiocyanate (FITC)-labeled lectin aliquoted (5 µg/mL) in CARBO-FREE® blocking solution. The FITC-labeled lectins VVA and WGA were purchased from purchased from EY Laboratories (San Mateo, Calif.) and SNA was purchased from Vector Laboratories (Burlingame, Calif.). After overnight incubation, washes were performed with 0.1% TRITON®-X-100 in 1× Tris-buffered saline (TBS). The lectin-stained slides were incubated in 0.3% Sudan Black in 70% ethanol solution to reduce autofluorescence. Slides were mounted with VECTASHIELD® containing the nuclear dye DAPI (Vector Laboratories) and digitally imaged with a Zeiss LSM 510 META confocal laser-scanning microscope (Carl Zeiss, Microimaging Inc., Thornwood, N.Y.). Images were acquired using a Plan-Apochromat 40× oil DIC objective. All images are 3D projections of confocal Z-stacks.

Figure 8B:
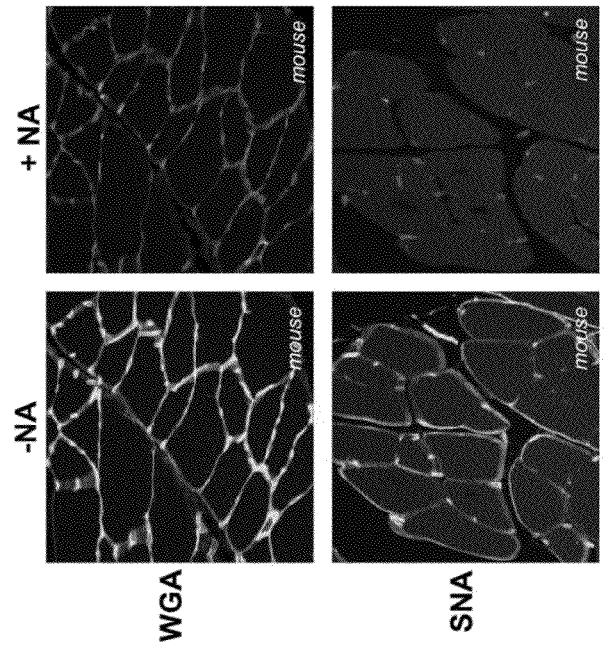
FIG. 8A-8B. Control histochemistry for WGA, SNA and VVA lectin specificity. Due to limited availability of control human muscle slides, wild type mouse (C57BL/6 strain) muscle (gastrocnemius and gluteus) slides were used to test specificity of the WGA, SNA lectins (used in FIG. 2). For specificity of VVA, GNE myopathy patient (GNE-21) muscle slides were used (since VVA does not bind to wild type mouse muscle glycans).
Figure 8A:
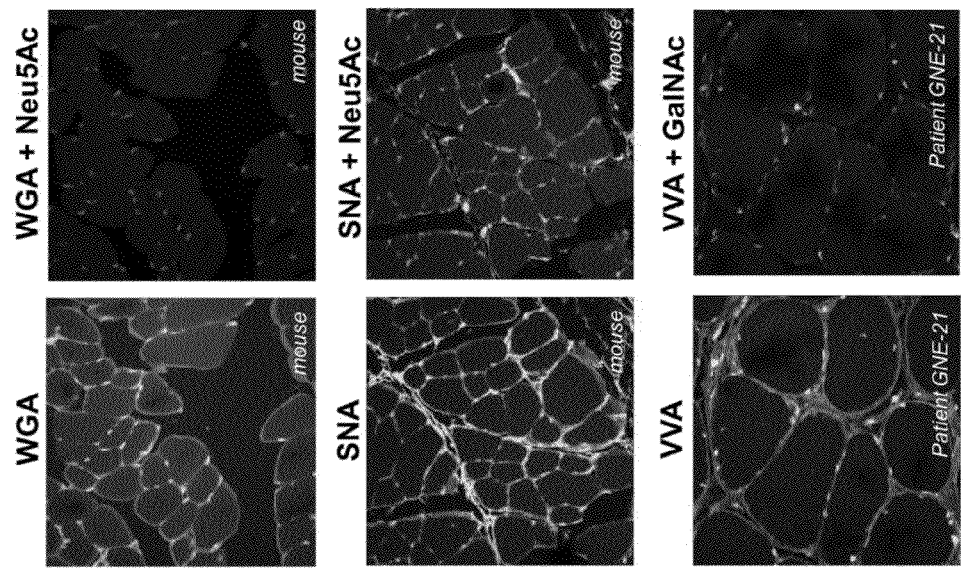

To verify lectin specificity (FIG. 8A-8B), each lectin was incubated with its specific inhibitory carbohydrate for 1 hour before overnight incubation on a slide. The inhibitory carbohydrates used were Neu5Ac (Toronto Research Chemicals, Toronto, Canada), for WGA and SNA, and GalNAc (Sigma-Aldrich) for VVA. In addition, tissue slides were desialylated by incubation with 5 µl (50 U) neuraminidase (P0720, New England Biolabs) for 1 hour at 37° C. in enzyme buffer.

Preparation and Permethylation of Plasma O-Linked Glycan Species:

O-linked glycan species were released from total (not albumin or IgG depleted) plasma or serum glycoproteins by β-elimination, essentially as described (Liu et al. *Mol Genet Metab* 106, 442-454 (2012); Carlson et al. *J Biol Chem* 243, 616-626 (1968); Faid et al. *Proteomics* 7, 1800-1813 (2007); Xia et al. *Anal Biochem* 442, 178-85 (2013)). Briefly, 10 μL of plasma was mixed with raffinose (1250 pmol in 5 μL) internal standard and 65 μl water for a final volume of 100 μL. To denature the plasma proteins and release the O-linked glycan species, the sample was mixed with 100 μL 2M sodium borate in 0.1M sodium hydroxide (freshly prepared) and incubated at 45° C. for 16 hours. Next, 1.6 mL of 0.25M acetic acid-methanol solution was drop wise added to neutralize the reaction, followed by O-glycan extraction with methanol. The extracted glycans were desalted through ion-exchange AG 50W-X8 resin (Bio-Rad, Hercules, Calif.) and lyophilized overnight.

For permethylation, four NaOH pellets (approximately 375 mg) were crushed in 10 mL anhydrous dimethyl sulfoxide (DMSO) with 0.5 μL water; 0.5 mL of this slurry and 0.2 mL $CH_3I$ were added to the dried glycans and the mixture was shaken vigorously for 1 hour, followed by five sequential chloroform/water (600 μL/200 μL) extractions from which the chloroform fractions were pooled. These combined chloroform phases were dried for 30 min under nitrogen (in chemical hood) and the permethylated O-glycan species were resuspended in 50 μL of 50% methanol and further purified through a C18 Stage Tip (Thermo Scientific, West Palm Beach, Fla.) as described (Guillard et al. *Clin Chem* 57, 593-602 (2011)).

O-Linked Glycan Analysis by LC-MS/MS and MALDI-TOF/TOF:

High performance liquid chromatography (HPLC) separation coupled with an electrospray ionization tandem mass spectrometry (LC-MS/MS) detection of 10 μA of each sample of permethylated O-glycan species was performed on a Shimadzu Prominence 20 AD LC and a Thermo GOLD™ 3-μm C18 column (2×100 mm), coupled with an ABSCIEX™ API-QTRAP® 5500 tandem mass spectrometer. The binary method used buffer A (acetonitrile:formic acid:water; 1:0.1:99 (v:v:v)) and buffer B (acetonitrile:formic acid:water; 99:0.1:1 (v:v:v)) with a flow rate at 0.25 mL/min under the following gradient conditions: 0-20 min, 50% to 80% buffer B; 20-28 min, 98% buffer B; 28-39 min, 50% buffer B. The API-QTRAP® 5500 tandem mass spectrometry conditions were as follows: ion source: EPI positive mode; curtain gas: 25; source temperature: 600. MRM transitions for core1 T-antigen (as determined by T-antigen standard) and sialyl-T-antigen (as determined by mass and fragmentation pattern) Yoo and Yoon, *Bull Korean Chem Soc* 26, 1347-1353 (2005)) were: m/z 534/298 and m/z 895/520. Calibration curves were constructed with 6 concentrations of T-antigen (from 0.0625 to 5 μM). The ST value is based on the ratio of the ST over the internal standard raffinose peak area, times the raffinose concentration.

The permethylated O-glycans were subsequently analyzed by matrix-assisted laser desorption-ionization (MALDI) time-of-flight (TOF) mass spectrometry on an Applied Biosystems MALDI-TOF/TOF 4800 Plus (Applied Biosystems, Foster City, Calif.) as described (Xia et al. *Anal Biochem* 442, 178-85 (2013)).

Results

Figure 7A:
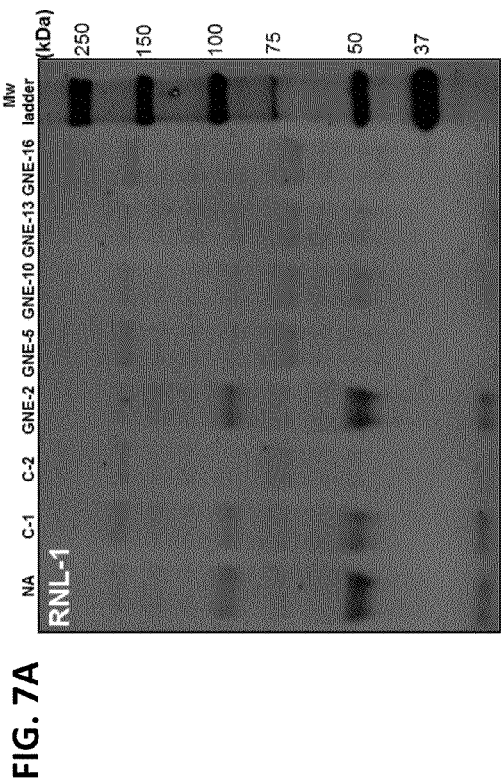
FIGS. 7A-7C. NCAM immunoblotting of serum glycoproteins. Serum samples (20 μg) from neuraminidase treated control (NA), control (C-1, C-2), and GNE myopathy patients were immunoblotted with the anti-NCAM antibodies (FIG. 7A) RNL-1 (sc-53007) and (FIG. 7B) H-300 (sc-10735) as described by Valles-Ayoub et al. *Genet. Test. Mol. Biomarkers.* 16(5), 313-317 (2012).
Figure 7B:
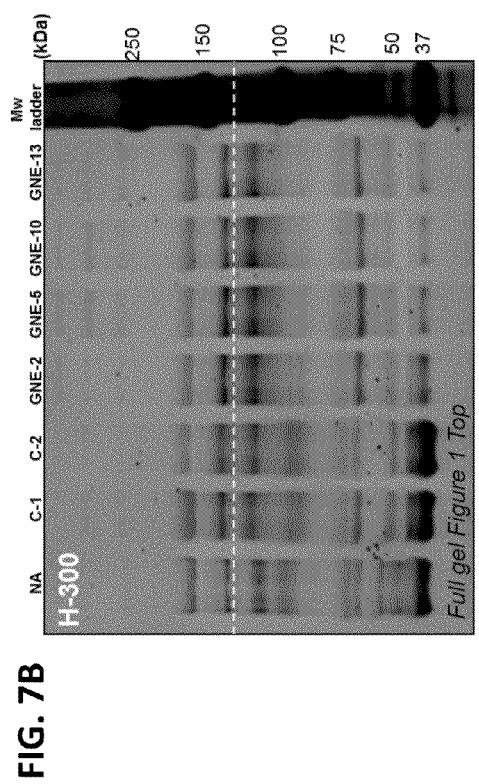
Figure 7C:
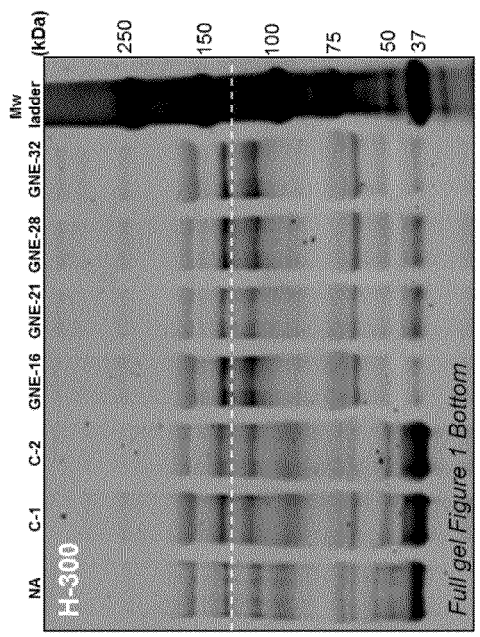

NCAM Immunoblotting:

Aberrantly sialylated NCAM, detected by immunoblotting of patients' serum, is the only previously suggested blood-based marker for GNE myopathy (Valles et al. *Genet Test Mol Biomarkers* 16, 313-317 (2012)) Immunoblotting of GNE myopathy serum was performed using the same conditions and NCAM (RNL-1; Santa Cruz Biotechnology) antibodies as previously employed (Valles et al., supra) but similar immunoresponsive bands were not observed (FIG. 7A). This may have been due to different sample handling or processing, or a different batch of the antibody than that used in the previous study. However, it was found that a different antibody to NCAM (H-300; Santa Cruz Biotechnology), detected all 3 major (~120, 140 and 180 kDa) isoforms of NCAM (Cunningham et al. *Science* 236, 799-806 (1987); Small et al. *J Cell Biol* 105, 2335-2345 (1987)) in human serum samples. Compared to control serum, all GNE myopathy patient serum samples demonstrated a slight downshift of the ~140 kDa NCAM isoform band, similar to a desialylated (by neuraminidase treatment) control sample (FIG. 4; FIG. 7B-7C). This downshift likely resulted from different electrophoretic mobility due to hyposialylation. The ~120 kDa and ~180 kDa isoforms do not appear to be desialylated in GNE myopathy serum samples.

Lectin Histochemistry and Lectin Blotting:

Staining with lectins (i.e., sugar-binding proteins with ligand specificities for defined carbohydrate sequences (Sharon, *J. Biol. Chem.* 282(5), 2753-2764 (2007)) was performed on normal and GNE myopathy muscle slides to examine the sialylation status. WGA (wheat germ agglutinin from *Triticum vulgaris*) predominantly recognizes terminal sialic acid (Sia) and N-acetylglucosamine (GlcNAc) on glycans (Sharon, supra; Iskratsch et al., *Anal. Biochem.* 386(2), 133-146 (2009); Kronis and Carver, *Biochemistry* 21(13), 3050-3057 (1982)) SNA (elderberry bark agglutinin from *Sambucus nigra*) predominantly recognizes terminal sialic acid (Sia) in an α(2,6)-linkage with either galactose (prevalent in N-linked glycans) or with N-acetylgalactosamine (GalNAc) (found in O-linked glycans) (Iskratsch et al., *Anal. Biochem.* 386(2), 133-146 (2009); Kronis et al., *Biochemistry* 21(13), 3050-3057 (1982); Shibuya et al., *J. Biol. Chem.* 262(4), 1596-1601 (1987)). VVA (hairy vetch agglutinin from *Vicia villosa*) predominantly binds GalNAc O-linked to serine or threonine residues of proteins (Iskratsch et al., op. cit.; Puri et al., *FEBS Lett* 312(2-3), 208-212 (1992)). Results of control experiments, indicating the specificity of each lectin, are presented in FIG. 8.

Figure 5:
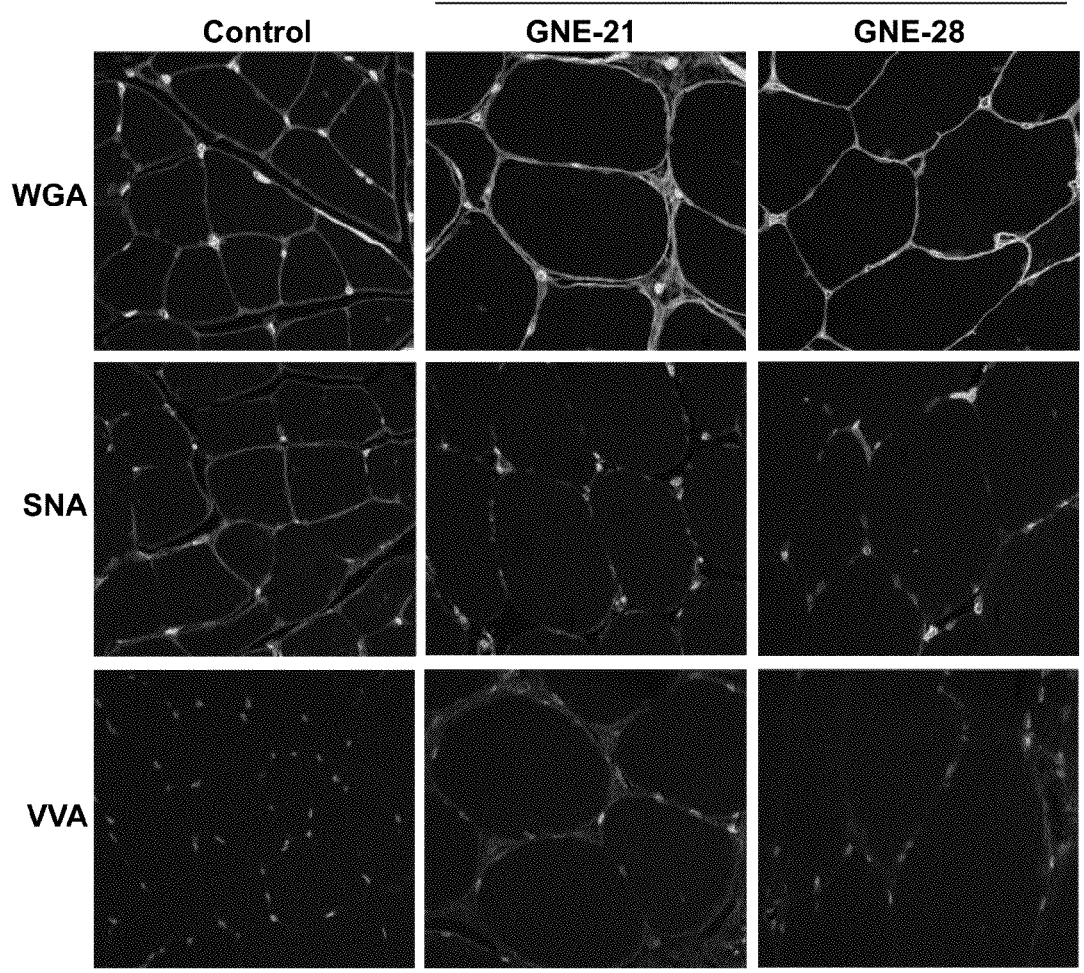
FIG. 5. Muscle lectin histochemistry. Paraffin-embedded muscle sections from biceps (control and GNE-28) and gastrocnemius (GNE-21) were stained with three lectins (light grey) informative for sialylation status and co-stained with the nuclear dye DAPI (dark grey). GNE myopathy muscle specimens show selective hyposialylation compared to control muscle, demonstrated by apparent normal staining of WGA (binding to most sialic acid groups), but decreased staining of SNA (predominantly binding terminal α(2,6)-linked sialic acid on all glycans). In addition, staining of VVA (predominantly binding terminal GalNAc, without sialic acid attached, O-linked to serine or threonine residues of glycoproteins) was increased in GNE myopathy muscle specimen compared to control, indicating hyposialylation of O-linked glycans. Specificity of the WGA, SNA and VVA lectins is demonstrated in FIG. 8.

GNE myopathy muscle, stained with WGA (recognizing most terminal sialic acids), showed a similar staining pattern as normal muscle (FIG. 5). However, staining with SNA (binding only α(2,6)-linked sialic acid) showed a markedly decreased signal in patients' muscle slides compared to normal, indicating that only specific sialylglycans are hyposialylated in GNE myopathy. VVA staining was almost absent in normal muscle since most glycans are sialylated, while GNE myopathy muscle showed a significant increase in staining compared to normal, indicating hyposialylation of O-linked glycans (FIG. 5).

Western blots were performed of controls, neuraminidase treated controls, and GNE myopathy serum proteins, and probed the blots with WGA, SNA or VVA (FIG. 9). While the neuraminidase treated control samples showed the expected reduction (for WGA and SNA) or increase (for VVA) in lectin binding, no significant differences in lectin binding could be identified in GNE myopathy patients' serum compared to control serum.

T/ST Ratios in GNE Myopathy Patients:

Plasma O-glycan species in control and GNE myopathy patients were analyzed by LC-MS/MS and MALDI-TOF/TOF. Five O-linked peaks were observed, at m/z 534, 895, 1256, 1344, and 1706 (FIG. 3A). The two major peaks in GNE myopathy patients represent the core 1 O-glycan species T-antigen (m/z 534) and the ST-antigen (m/z 895) (Faid et al., *Proteomics* 7(11), 1800-1813 (2007); Xia et al., *Anal. Biochem.* 442(2), 178-85 (2013)). The relative quantities of T and monosialylated ST antigens were measured using the LC-MS/MS method by comparing their intensities to the internal standard raffinose at m/z 681 (Table 5, Table 6 as well as using purified T-antigen as external standard to further validate T-antigen quantities. Except for purified T-antigen, there are no purified standards of other O-glycan species (e.g., ST-antigen (m/z 895), m/z 1256, 1344 peaks) commercially available at this time. To evaluate the sialylation of core 1 O-glycan species per patient, the ratio between T- and monosialylated ST-antigen was obtained. Fifty control samples (from the normal plasma collection at the Emory Biochemical Genetics Laboratory) were measured to establish a normal range for both T-antigen (0.280-1.398 µM), monosialylated ST antigen (14.145-30.373 µM) and the T/ST ratio (<0.052), similar ranges as recently previously described (Xia et al., supra). An additional 5 control plasma samples from the NM blood bank were in the normal range for T-antigen, monosialylated ST-antigen and the T/ST ratio.

In GNE myopathy plasma, one of the absolute values of either T- or monosialylated ST-antigen often appeared within the normal range, but the T/ST ratio was consistently abnormal (>0.052, note all abnormal samples are >0.06) in all analyzed plasma samples from untreated patients (FIG. 6B; Table 6; Table 5). Importantly, the T/ST ratio of one of the untreated GNE myopathy patients was abnormal (GNE-914a; T/ST=0.100), but shifted to the normal range 24 hours after intravenous immunoglobulin (IVIG) therapy on two consecutive days (GNE914b; T/ST=0.0454).

TABLE 6

Mutations and plasma T and monosialylated ST values of GNE myopathy patients.

| Patient | GNE allele 1 | GNE allele 2 | T/ST | T (uM) | ST (uM) |
|---|---|---|---|---|---|
| | | | Normal Range | | |
| | | | <0.052 | 0.280-1.14 | 14.1-30.3 |
| GNE-2 | c. 1909 + 5G > A | p.V696M | 0.107 | 1.34 | 12.6 |
| GNE-5 | p.M712T | p.M712T | 0.073 | 1.02 | 14.0 |
| GNE-10 | p.D213V | v.V696M | 0.105 | 1.24 | 11.8 |
| GNE-13 | p.M712T | p.M712T | 0.134 | 1.09 | 8.10 |
| GNE-14 | p.V216A | p.A631V | 0.069 | 0.85 | 12.2 |
| GNE-16 | p.M712T | p.M712T | 0.099 | 1.66 | 16.7 |
| GNE-20 | p.W513X | p.A631V | 0.077 | 1.18 | 15.3 |
| GNE-21 | p.D378Y | p.A631V | 0.085 | 0.89 | 10.4 |
| GNE-28 | p.R129X | p.V696M | 0.091 | 1.56 | 17.1 |
| GNE-32 | p.M712T | p.M712T | 0.065 | 0.98 | 14.9 |
| GNE-980 | p.M712T | p.M712T | 0.102 | 1.37 | 13.3 |
| GNE-981 | p.M712T | p.M712T | 0.112 | 1.53 | 13.7 |
| GNE-914a[1] | p.M712T | p.M712T | 0.100 | 0.22 | 2.20 |
| GNE-914b[2] | p.M712T | p.M712T | 0.045* | 0.40 | 8.85 |

Gray highlight: Abnormal value
[1]GNE-914a = plasma value before administration of IVIG
[2]GNE-914b = plasma value 24 h after IVIG therapy Multiple plasma and also serum samples, including samples that were collected from the same patients at different time-points (baseline and 3, 6, and/or 9 months after baseline), were tested from selected patients. These samples did not show significant differences in the T/ST ratios (Table 7), indicating that plasma as well as serum can be used for this assay and that the assay is reproducible.

TABLE 7

Plasma and serum T, monosialylated ST and T/ST ratio values at different time points in selected patients

| Patient | Time point[1] | T/ST | T (uM) | ST (uM) |
|---|---|---|---|---|
| | | Normal Plasma Range | | |
| | | <0.052 | 0.280-1.14 | 14.1-30.3 |
| GNE-2 | baseline | 0.107 | 1.34 | 12.6 |
| | 3 months | 0.087 | 1.27 | 14.6 |
| | 6 months | 0.137 | 1.77 | 12.9 |
| | Serum baseline[2] | 0.131 | 2.25 | 17.2 |
| GNE-10 | baseline | 0.105 | 1.24 | 11.8 |
| | 3 months | 0.097 | 1.79 | 18.5 |
| | 6 months | 0.102 | 1.44 | 14.1 |
| | Serum baseline | 0.129 | 2.46 | 19.0 |
| GNE-13 | baseline | 0.134 | 1.09 | 8.11 |
| | 3 months | 0.066 | 1.14 | 17.3 |
| | 9 months | 0.071 | 0.85 | 12.0 |
| GNE-14 | baseline | 0.069 | 0.85 | 12.2 |
| | 6 months | 0.089 | 1.34 | 15.0 |
| GNE-32 | baseline | 0.065 | 0.98 | 14.9 |
| | Serum baseline | 0.105 | 2.39 | 22.7 |

[1]Baseline = timepoint of first blood draw; 3, 6, 9 months = timepoints of subsequent blood draws after baseline.
[2]Serum baseline = T, ST and T/ST ratio values determined in serum from each patient at the baseline blood draw.

Major bathers to the diagnosis of GNE myopathy have been the rarity of the disease and the lack of an inexpensive and noninvasive diagnostic test. Most GNE myopathy patients escape diagnosis, with a typical diagnostic delay of approximately 10 years after onset of symptoms (Huizing M. et al., GNE Myopathy. *Scriver's Online Metabolic and Molecular Bases of Inherited Disease. ommbid.com* (258), (2013)). This leads to anxiety and unnecessary testing, often involving an invasive muscle biopsy (Noguchi et al., *J. Biol. Chem.* 279(12), 402-11407 (2004); Tajima et al., *Am. J. Pathol.* 166(4), 1121-1130 (2005); Huizing et al., *Mol. Genet. Metab.* 81(3), 196-202 (2004); Broccolini et al., *J. Neurochem.* 105(3), 971-981 (2008); Ricci et al, *PLoS One* 5(4), e10055 (2010)). As an alternative, blood-based markers were explored to aid in diagnosis and monitoring response to therapy.

Figure 4:
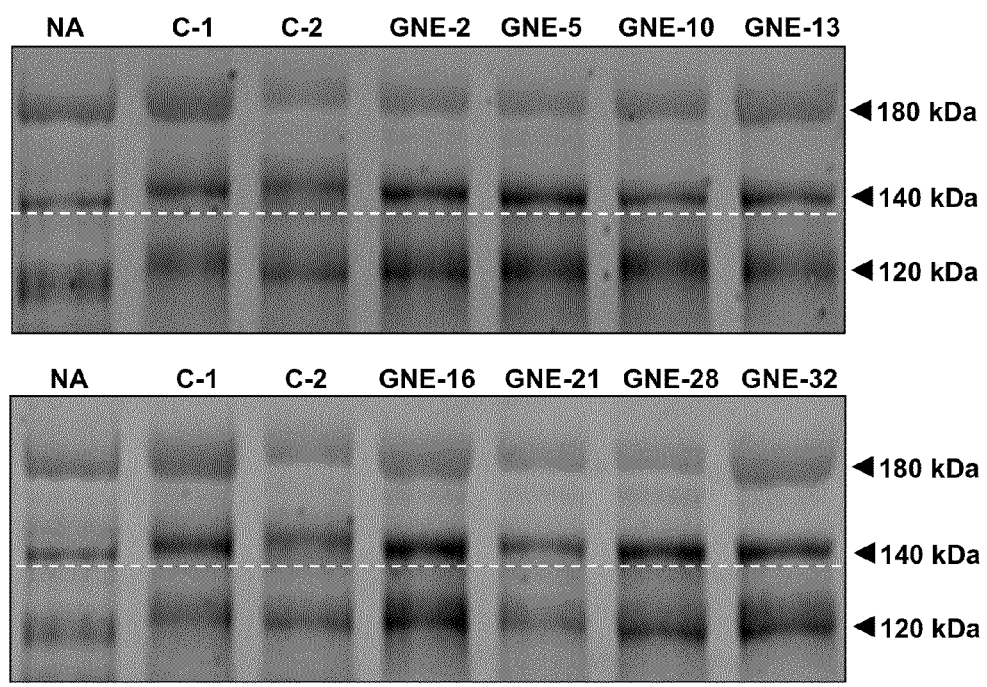
FIG. 4. NCAM (H-300) immunoblotting of serum glycoproteins. Serum samples (20 μg) from neuraminidase treated control (NA), control (C-1, C-2), and GNE myopathy patients (see Table 6 for details) were immunoblotted with NCAM antibodies (H-300; sc-10735). Compared to control, serum from GNE myopathy patients showed a slight downshift of the 140 kDa NCAM isoform. A similar downshift was present in neuraminidase treated control serum (NA). Dotted line is to aid in discerning migration. See FIG. 7B for the full gel images.

Sialylation on NCAM detected by immunochemistry was suggested as a muscle- (Broccolini et al., *Neurology* 75(3), 265-272 (2010)) and blood-based marker for GNE myopathy patients (Valles et al. *Genet Test Mol Biomarkers* 16(5), 313-317 (2012)), but results may vary with the antibodies used, since NCAM has several membrane bound and soluble tissue-specific isoforms (Cunningham et al., *Science* 236(4803): 799-806 (1987); Small et al., *J. Cell. Biol.* 105(5), 2335-2345 (1987)). The application of a reported informative NCAM antibody (RNL-1, (Valles et al., op. cit.) in GNE myopathy serum samples did not show reproducible data (FIG. 7A-7C), possibly related to differences in sample processing or antibody batch. However, the tests with another NCAM antibody (H-300) showed reactivity for all three major NCAM isoforms in human serum samples. GNE myopathy patients' sera showed a slight down-shift of the 140 kDa NCAM isoform, indicating a possible difference of sialylation on NCAM, resulting in different gel mobility in GNE myopathy patients (FIG. 4). Interestingly, a downshift of the ~140 kDa NCAM isoform was previously reported in muscle extracts of GNE myopathy patients (Ricci et al, *Neurology* 66(5), 755-758 (2006); Broccolini et al., op. cit.) indicating a possible link of this isoform to the disease. The ~120 kDa and ~180 kDa isoforms of serum NCAM appeared not informative for diagnosis of GNE myopathy. Optimizing specificity and sensitivity of the immunoreactive ~140 kDa NCAM band in human serum could be informative for GNE myopathy.

Predominantly hyposialylated O-linked glycans are present in GNE myopathy (Tajima et al., *Am. J. Pathol.* 166 (4), 1121-1130 (2005); Huizing et al., *Mol. Genet. Metab.* 81(3), 196-202 (2004; Nemunaitis et al. *Hum. Gene Ther.* 22(11), 1331-1341 (2011); Niethamer et al., *Mol. Genet. Metab.* 107(4), 748-755 (2012)). In the studies disclosed herein, analysis of O-linked glycan structures in the plasma were analyzed by a recently developed semi-quantitative method that determines the ratio of the T- and ST-antigens (T/ST) (Xia et al., *Anal. Biochem.* 442(2), 178-85 (2013)). Using this method, mild undersialylation of plasma 0-linked glycan species was demonstrated in all tested GNE myopathy patients, resulting in abnormally high T/ST ratios (>0.052; Table 6). Determining the T/ST ratios in GNE myopathy proved robust and superior to solely semi-quantifying and comparing only the individual T- and ST-antigen values; while individual T- and ST-antigen values can be in the normal range in some GNE myopathy patients (Table 6), the T/ST ratio was abnormal (>0.052) in all untreated patients. Serum samples from selected GNE myopathy patients showed similar T/ST ratios (results not shown) to the corresponding plasma samples, indicating that either serum or plasma can be used for this assay.

The fact that some GNE myopathy patients have normal values of T- or ST-antigen indicates that their undersialylation of O-linked glycan species is likely mild. It is possible that due to defects in GNE enzyme activities (Noguchi et al., *J. Biol. Chem.* 279(12), 11402-11407 (2004); Sparks et al., *Glycobiology* 15(11), 1102-1110 (2005)), a gradual defect in de novo sialic acid production occurs in GNE myopathy patients. Some glycans may be preferentially (under)sialylated, perhaps based on (tissue-specific) substrate affinity, protein-specific transport pathways through the Golgi-complex for sialylation, expression of certain sialyltransferases or neuraminidases, or other mechanisms (Harduin-Lepers et al., *PLoS One* 7(8), e44193 (2012); Giacopuzzi et al., *PLoS One* 7(8), e44193 (2012); Pshezhetsky et al., *Biochemistry* (Mosc) 78(7), 736-745 (2013)). The gradual shortage of tissue-, protein, or sialyl linkage-specific sialylation of predominantly O-linked glycans may play a role in the adult onset and muscle specific symptoms of GNE myopathy. Proteins with significant O-linked glycosylation may largely be affected and contribute to the phenotype. In this cohort of GNE myopathy patients, there was no direct correlation of T/ST plasma ratios to severity and onset of the disease, nor to GNE gene mutations (Table 6).

Unfortunately, it is difficult to identify GNE myopathy patients before the onset of symptoms, but the evaluation of T/ST ratios in such non-symptomatic patients may indicate the usefulness of T/ST ratios as an early diagnostic tool for the disease.

The presence of T-antigen, Tn-antigen and STn-antigens was utilized as markers for certain cancers. Absolute T-, ST-, Tn-, and STn-antigen values are significantly altered in different forms or stages of cancers (Springer et al., *J. Mol. Med.* (*Berl*) 75(8), 594-602 (1997); Cao et al., *Cancer* 76(10), 1700-1708 (1995); Goletz et al., *Adv. Exp. Med. Biol.* 535, 147-162 (2003); Imai et al., *Anticancer Res.* 21(2B), 1327-1334 (2001)) but their ratios (including T/ST) are rarely used in cancer research. T/ST ratios were informative in patients with classic galactosemia (galactose-1-phosphate uridylyltransferase (GALT)-deficiency (Liu et al. *Mol Genet Metab* 106, 442-454 (2012)).

Most such glycosylation disorders present with severe congenital clinical phenotypes, much different from adult onset GNE myopathy. Early clinical symptoms of GNE myopathy (waddling gait, foot drop) are non-specific features of various neurological/muscular disorders and contribute to the delayed diagnosis of patients. Such early symptoms in combination with abnormal plasma T/ST ratios can be indicators for GNE mutation testing, which will ultimately confirm the diagnosis of GNE myopathy.

Sialylation-increasing therapies could normalize the plasma T/ST ratios in GNE myopathy patients, and possibly indicate response to therapy. Currently, no therapies are currently approved for GNE myopathy. Plasma samples were acquired from one GNE myopathy patient who was part of a previously conducted pilot clinical trial of intravenous supplementation of sialylated compounds in the form of immune globulins (IVIG; (see the website clinicaltrials.gov/ identifier: NCT00195637) (Sparks et al., *BMC Neurol.* 7, 3 (2007)). The sialic acid residues on IgG (~8 mmol of sialic acid/g) could presumably be recycled to sialylate other glycans. While this study showed improvement in strength of different muscle groups and notable subjective improvement reported by the patients, no biochemically relevant evidence of re-sialylation was detected. Plasma from the patient before therapy had an abnormal T/ST value (0.100), while a plasma sample acquired 24 h after 1 g/kg IVIG loading on two consecutive days showed a normalized T/ST ratio (0.045). Human IVIG is N-glycosylated and does not contain O-linked glycans. Therefore the potential presence of residual, non-degraded IgG in the patient's plasma did not directly contribute to the ST-value after therapy. The increased ST values and decreased T/ST ratios after therapy suggest that sialic acids on the loaded IgG were processed/recycled to create sialylation of T-antigens on other glycans. Thus, plasma T/ST ratios could be used for response to therapy in GNE myopathy patients.

Other substrate replacement therapies for GNE myopathy patients are currently in exploratory stages, and include oral supplementation of sialic acid itself (see the clinicaltrials.gov website) identifiers: NCT01634750, NCT01236898, and NCT01517880) and oral supplementation of the sialic acid precursor N-acetylmannosamine (ManNAc) (see the clinicaltrials.gov website, identifier: NCT01634750). The T/ST ratios can be used for gauging response to these therapies.

Thus, it was demonstrated that the ratio of the Thomsen-Friedenreich (T)-antigen to its sialylated form, ST-antigen, detected mass spectrometry, for example semi-quantitative LC-MS/MS and MALDI-TOF/TOF, is a robust blood-based (serum or plasma) biomarker informative for diagnosis and for response to therapy for GNE myopathy. In addition, the specific hyposialylation of core 1 O-linked glycan species can aid in elucidating the pathology and adult onset clinical symptoms of GNE myopathy.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. A method for confirming the diagnosis of a hyposialylation disorder in a subject, comprising
   permethylating glycans in a biological sample from the subject;
   performing mass spectrometry to measure monosialylated Thomsen-Friedenreich (ST) antigen and non-sialylated Thomsen-Friedenreich antigen (T) from the biological sample, wherein Thomsen-Friedenreich antigen is N-acetylgalactosamine (GalNAc) linked to galactose (Gal); and
   determining the ratio of T to ST;
   wherein a ratio of T to ST of about 0.06 or greater confirms the diagnosis of the hyposialylation disorder, wherein the hyposialylation disorder is GNE myopathy.

2. The method of claim 1, further comprising
   detecting a ratio of T to ST greater than about 0.06; and
   administering to the subject a therapeutic agent for the treatment of the hyposialylation disorder.

3. The method of claim 1, further comprising comparing the T/ST ratio to a control, wherein the control is the ratio of T to ST in a sample from a subject known not to have GNE myopathy.

4. A method of determining the effectiveness of a first dosage of a therapeutic agent for treatment of a hyposialylation disorder in a subject, comprising
   permethylating glycans from a biological sample from the subject;
   performing mass spectrometry to detect monosialylated Thomsen-Friedenreich (ST) antigen and non-sialylated Thomsen-Friedenreich antigen (T) from the biological sample from the subject, wherein Thomsen-Friedenreich antigen is N-acetylgalactosamine (GalNAc) linked to galactose (Gal); and
   determining the ratio of T to ST;
   wherein a ratio of T to ST of less than about 0.06 indicates that the first dosage of the therapeutic agent is effective for the treatment of the hyposialylation disorder, and a ratio of T to ST of about 0.06 or greater indicates that the first dosage of the therapeutic agent is not effective for the treatment of the hyposialylation disorder.

5. The method of claim 4, further comprising administering to the subject a second dosage of the therapeutic agent,
   wherein a ratio of T to ST of less than about 0.06 indicates that the second dosage of the agent is effective for the treatment of the subject,
   and wherein a ratio of T to ST of about 0.06 or greater indicates that the second dosage of the therapeutic agent is not effective for the treatment of the subject.

6. The method of claim 4, wherein the therapeutic agent is N-acetyl-D-mannosamine (ManNAc), N-acetylneuraminic acid (Neu5Ac), sialic acid, mannosamine, or one or more sialylated compounds.

7. The method of claim 6, wherein the one or more sialylated compounds comprises intravenous immunoglobulin (IVIG) or sialyllactose.

8. The method of claim 5, wherein the first dosage of the therapeutic agent and the second dosage of the therapeutic agent are different.

9. The method of claim 4, wherein the therapeutic agent is an extended release formulation or is encapsulated.

10. The method of claim 4, wherein detecting monosialylated Thomsen-Friedenreich (ST) antigen and non-sialylated Thomsen-Friedenreich (T) antigen comprises
    detecting the mass transition between a parent ion and fragment ion of the T antigen and a parent ion and fragment ion of the ST antigen.

11. The method of claim 10, wherein
    a) a parent ion m/z of the T antigen is 534, a parent ion m/z of the monosialylated ST antigen is 895, and the fragment ions are 298 and 520, respectively; and/or
    b) wherein multiple reaction monitoring (MRM) transitions for T-antigen is m/z 534/298 and for monosialylated ST-antigen is m/z 895/520.

12. The method of claim 10, wherein detecting the mass transition using mass spectrometry provides the relative ratio of T to monosialylated ST antigens.

13. The method of claim 10, wherein the mass spectrometry is matrix assisted laser desorption ionization time of flight (MALDI-TOF) mass spectrometry or liquid chromatography (LC)-mass spectrometry.

14. The method of claim 13, wherein the mass spectrometry is MALDI-TOF mass spectrometry and wherein the method comprises
    releasing O-glycans from the biological sample;
    desalting the O-glycans; and then
    permethylating the O-glycans prior to MALDI-TOF mass spectrometry.

15. The method of claim 14, wherein releasing O-glycans comprises treating the biological sample with sodium hydroxide and sodium borohydrate.

16. The method of claim 14, wherein desalting the O-glycans comprises using ion-exchange chromatography.

17. The method of claim 4, wherein the biological sample is a plasma sample or a serum sample.

18. A method of detecting monosialylated Thomsen-Friedenreich (ST) antigen and non-sialylated Thomsen-Friedenreich antigen (T) in a biological sample from a subject, comprising:
    permethylating glycans from a biological sample comprising ST antigen and T antigen from a subject, thereby forming a permethylated sample;
    performing matrix assisted laser desorption ionization time of flight (MALDI-TOF) mass spectrometry to measure monosialylated Thomsen-Friedenreich (ST) antigen and non-sialylated Thomsen-Friedenreich antigen (T) from the permethylated sample, wherein
    a) a parent ion m/z of the T antigen is 534, a parent ion m/z of the monosialylated ST antigen is 895, and the fragment ions are 298 and 520, respectively; and/or
    b) wherein multiple reaction monitoring (MRM) transitions for T-antigen is m/z 534/298 and for monosialylated ST-antigen is m/z 895/520,
    thereby detecting ST and T antigen,
    wherein Thomsen-Friedenreich antigen is N-acetylgalactosamine (GalNAc) linked to galactose (Gal), and wherein the subject has GNE myopathy.

19. The method of claim 18, comprising releasing O-glycans from the biological sample;
    desalting the O-glycans; and then
    permethylating the O-glycans to form the permethylated sample.

* * * * *